United States Patent
Fennell et al.

(10) Patent No.: US 10,036,734 B2
(45) Date of Patent: Jul. 31, 2018

(54) ULTRASONIC SENSOR WITH BONDED PIEZOELECTRIC LAYER

(71) Applicant: SnapTrack, Inc., San Diego, CA (US)

(72) Inventors: Leonard Eugene Fennell, San Jose, CA (US); Nicholas Ian Buchan, San Jose, CA (US); David William Burns, San Jose, CA (US); Kostadin Dimitrov Djordjev, San Jose, CA (US); Stephen Michael Gojevic, Lockport, NY (US); Jack Conway Kitchens, II, Buffalo, NY (US); John Keith Schneider, Williamsville, NY (US); Nathaniel Robert Bennett, Menlo Park, CA (US); Kristopher Andrew Lavery, Pleasonton, CA (US)

(73) Assignee: SNAPTRACK, Inc., San Diego, CA (US)

( * ) Notice: Subject to any disclaimer, the term of this patent is extended or adjusted under 35 U.S.C. 154(b) by 721 days.

(21) Appl. No.: 14/293,841

(22) Filed: Jun. 2, 2014

(65) Prior Publication Data
US 2014/0352440 A1 Dec. 4, 2014

Related U.S. Application Data

(60) Provisional application No. 61/830,615, filed on Jun. 3, 2013.

(51) Int. Cl.
*G06K 9/24* (2006.01)
*G01N 29/22* (2006.01)
(Continued)

(52) U.S. Cl.
CPC ........... *G01N 29/22* (2013.01); *G06K 9/0002* (2013.01); *H01L 41/25* (2013.01); *Y10T 29/42* (2015.01)

(58) Field of Classification Search
CPC ...... G01N 29/09; G01N 29/28; G01N 29/223; G01N 29/2468; G01N 29/2462;
(Continued)

(56) References Cited

U.S. PATENT DOCUMENTS

| 7,223,243 B2 | 5/2007 | Morris et al. |
| 7,400,750 B2 | 7/2008 | Nam |

(Continued)

FOREIGN PATENT DOCUMENTS

| CN | 101315823 A | 12/2008 |
| CN | 101533170 | 9/2009 |

(Continued)

OTHER PUBLICATIONS

International Search Report and Written Opinion—PCT/US2014/040746—ISA/EPO—Nov. 12, 2014.
(Continued)

*Primary Examiner* — Hezron E Williams
*Assistant Examiner* — Rose M Miller
(74) *Attorney, Agent, or Firm* — Weaver Austin Villeneuve & Sampson LLP-QUAL

(57) ABSTRACT

This disclosure provides systems, methods and apparatus related to an ultrasonic sensor for detecting ultrasonic energy. In some implementations, the ultrasonic sensor includes a piezoelectric receiver layer bonded with an adhesive to an array of pixel circuits disposed on a substrate, each pixel circuit in the array including at least one thin film transistor (TFT) element and having a pixel input electrode electrically coupled to the pixel circuit. Methods of forming ultrasonic sensors include bonding piezoelectric receiver layers to TFT arrays.

19 Claims, 26 Drawing Sheets

(51) Int. Cl.
*H01L 41/25* (2013.01)
*G06K 9/00* (2006.01)

(58) Field of Classification Search
CPC .......... G01N 2291/018; G06K 9/0002; G06K 9/00013; G10K 11/02
USPC .......... 73/589, 602, 617, 644, 627, 628, 629
See application file for complete search history.

(56) References Cited

U.S. PATENT DOCUMENTS

| | | | |
|---|---|---|---|
| 7,616,786 B2 | 11/2009 | Setlak | |
| 7,955,641 B2 | 6/2011 | Schneider et al. | |
| 8,139,827 B2* | 3/2012 | Schneider | G01N 29/06 382/123 |
| 8,183,745 B2 | 5/2012 | Trolier-McKinstry et al. | |
| 8,193,685 B2 | 6/2012 | Klee et al. | |
| 8,201,739 B2 | 6/2012 | Schneider et al. | |
| 8,247,802 B2 | 8/2012 | Nomura et al. | |
| 8,288,776 B2 | 10/2012 | Choi et al. | |
| 8,724,832 B2 | 5/2014 | Stephanou et al. | |
| 9,262,003 B2 | 2/2016 | Kitchens et al. | |
| 2006/0286311 A1 | 12/2006 | Okazaki et al. | |
| 2007/0029899 A1 | 2/2007 | Matsuzawa | |
| 2007/0089525 A1 | 4/2007 | Momose et al. | |
| 2007/0231462 A1 | 10/2007 | Araki et al. | |
| 2007/0258628 A1* | 11/2007 | Schneider | A61B 5/1172 382/124 |
| 2007/0272020 A1 | 11/2007 | Schneider et al. | |
| 2008/0033298 A1 | 2/2008 | Habu et al. | |
| 2008/0231145 A1 | 9/2008 | Nagano et al. | |
| 2010/0052478 A1* | 3/2010 | Schneider | B06B 1/0688 310/334 |
| 2011/0034912 A1 | 2/2011 | De Graff et al. | |
| 2011/0112622 A1 | 5/2011 | Phan et al. | |
| 2011/0215150 A1* | 9/2011 | Schneider | G06K 9/0002 235/439 |
| 2011/0279662 A1 | 11/2011 | Schneider et al. | |
| 2012/0111119 A1 | 5/2012 | Small et al. | |
| 2012/0144920 A1 | 6/2012 | Wong et al. | |
| 2012/0147698 A1 | 6/2012 | Wong et al. | |
| 2013/0201134 A1 | 8/2013 | Schneider et al. | |
| 2014/0035935 A1 | 2/2014 | Shenoy et al. | |
| 2014/0198072 A1 | 7/2014 | Schuele et al. | |
| 2014/0354596 A1* | 12/2014 | Djordjev | G06K 9/0002 345/175 |
| 2014/0354597 A1* | 12/2014 | Kitchens, II | G06F 1/3215 345/175 |
| 2014/0354905 A1* | 12/2014 | Kitchens | G06F 1/3215 349/12 |
| 2014/0355387 A1* | 12/2014 | Kitchens, II | H04R 17/005 367/137 |
| 2014/0359757 A1* | 12/2014 | Sezan | G06F 21/32 726/19 |
| 2015/0123931 A1* | 5/2015 | Kitchens | G06F 3/0414 345/174 |
| 2015/0241393 A1* | 8/2015 | Ganti | G01N 29/09 73/589 |
| 2015/0286318 A1 | 10/2015 | Morein et al. | |
| 2016/0026842 A1 | 1/2016 | Withers et al. | |
| 2016/0171276 A1 | 6/2016 | Chiang et al. | |
| 2016/0210496 A1 | 7/2016 | Lin et al. | |
| 2017/0364726 A1 | 12/2017 | Buchan et al. | |

FOREIGN PATENT DOCUMENTS

| | | |
|---|---|---|
| CN | 101691202 A | 4/2010 |
| CN | 102596044 A | 7/2012 |
| DE | 19833928 A1 | 2/2000 |
| JP | S58186981 | 11/1983 |
| JP | 2012125560 | 7/2012 |
| JP | 2012127945 | 7/2012 |
| KR | 20010110247 A | 12/2001 |
| KR | 100363279 | 2/2003 |
| KR | 20080109327 A | 12/2008 |
| TW | 200625155 A | 7/2006 |
| WO | WO-2008015917 A1 | 2/2008 |
| WO | 2015/105320 A1 | 7/2015 |

OTHER PUBLICATIONS

Partial International Search Report—PCT/US2014/040746—ISA/EPO—Aug. 28, 2014.

Lee J.S., et al., "Surface Functionalization of a Poly(vinylidene fluoride): Effect on the Adhesive and Piezoelectric Properties", ACS Applied Materials & Interfaces, 2009, vol. 1 (12), pp. 2902-2908.

Pecora A., et al., "Flexible PVDF-TrFE pyroelectric Sensor Driven by Polysilicon Thin Film Transistor Fabricated on Ultra-Thin Polyimide Substrate", Sensors and Actuators A: Physical, 2012, vol. 185, pp. 39-43.

Serrado Nunes. J., et al., "Electrical and Microstructural Changes of P-PVDF under Different Processing Conditions by Scanning Force Microscopy," Materials Research Society Symposium Proceedings, 2007, vol. 949, pp. 1-6.

Xu H., et al., "Domain Stabilization Effect of Interlayer on Ferroelectric Poly(Vinylidene Fluoride-Trifluoroethylene) Copolymer Ultrathin Film," Journal of Applied Physics, 2009, vol. 105 (3), pp. 34107-1-34107-6.

Taiwan Search Report, Taiwan Application No. TW103119261, dated Oct. 23, 2017.

Pangracious V., et al., "Three-Dimensional Integration: A More Than Moore Technology", In: Three-Dimensional Design Methodologies for Tree-based FPGA-Architecture, Jan. 1, 2015, vol. 350, Springer, XP055405152, pp. 13-41.

Wang, Z., "3-D Integration and Through-Silicon Vias in MEMS and Microsensors", Journal of Microelectromechanical Systems, Oct. 1, 2015, vol. 24, No. 5, XP055405155, pp. 1211-1244.

International Preliminary Report on Patentability—PCT/US2014/039985, The International Bureau of WIPO—Geneva, Switzerland, dated Sep. 17, 2015.

International Preliminary Report on Patentability—PCT/US2014/040746, The International Bureau of WIPO—Geneva, Switzerland, dated Sep. 16, 2015.

International Search Report and Written Opinion—PCT/US2014/039985—ISA/EPO—dated Nov. 20, 2014.

International Search Report and Written Opinion—PCT/US2017/035981—ISA/EPO—dated Sep. 19, 2017.

International Written Opinion—PCT/US2014/039985—dated Jun. 8, 2015.

PCT/US2014/039985—ISA/EPO—dated Sep. 17, 2014. Invitation to Pay Additional Fees.

* cited by examiner

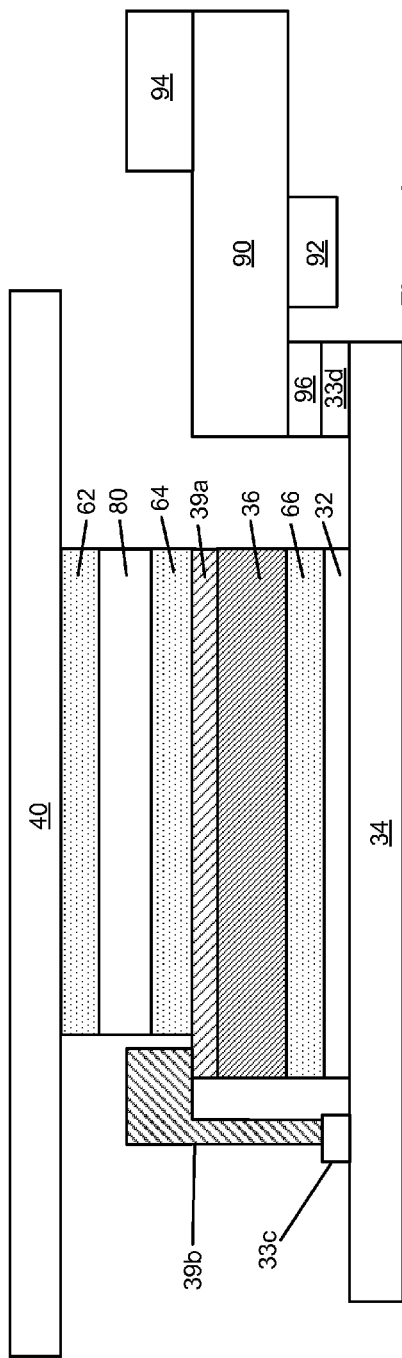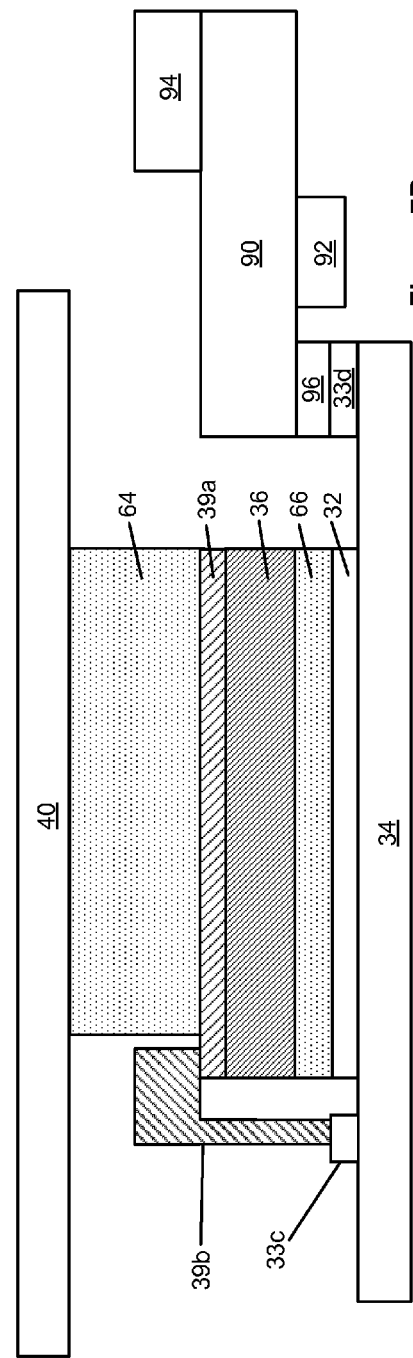

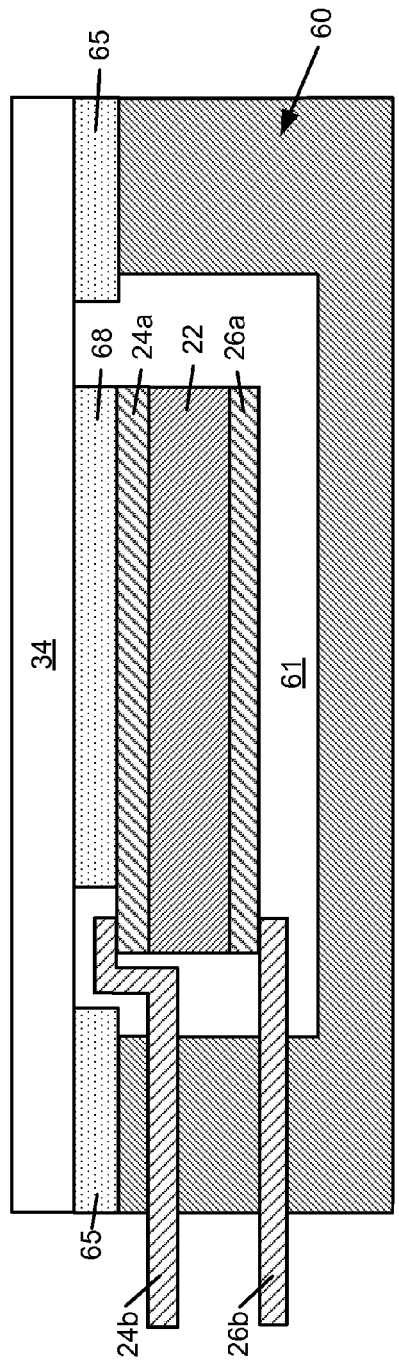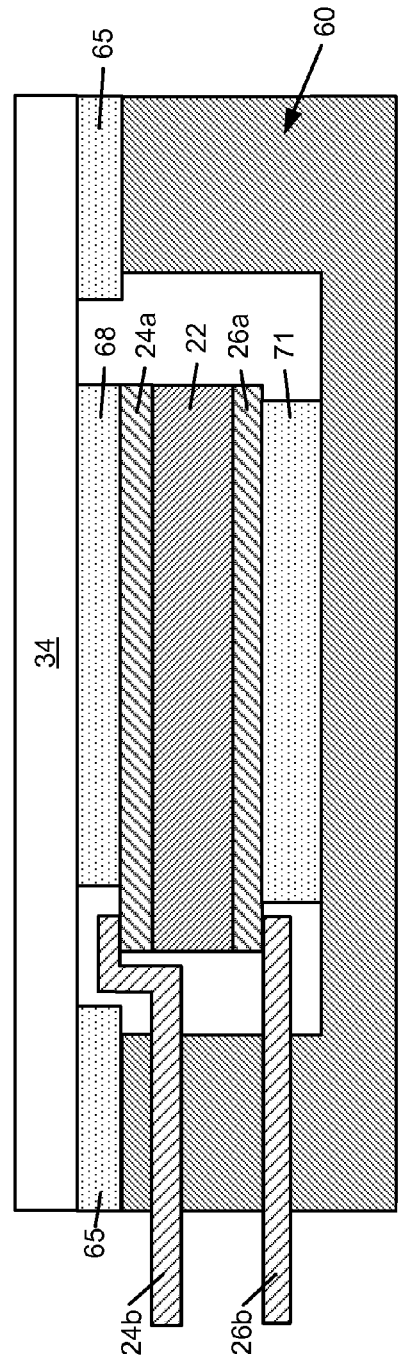

ULTRASONIC SENSOR WITH BONDED PIEZOELECTRIC LAYER

CROSS-REFERENCE TO RELATED APPLICATION

This disclosure claims priority under 35 U.S.C. § 119 to U.S. Provisional Patent Application No. 61/830,615, filed Jun. 3, 2013, entitled "ULTRASONIC SENSOR WITH BONDED PIEZOELECTRIC LAYER." The disclosure of the prior application is considered part of, and is incorporated by reference in, this disclosure for all purposes.

TECHNICAL FIELD

This disclosure relates generally to ultrasonic sensors and more particularly to ultrasonic sensor arrays including piezoelectric transmitters and receivers.

DESCRIPTION OF THE RELATED TECHNOLOGY

In an ultrasonic sensor system, an ultrasonic transmitter may be used to send an ultrasonic wave through an ultrasonically transmissive medium or media and towards an object to be detected. The transmitter may be operatively coupled with an ultrasonic sensor array configured to detect portions of the ultrasonic wave that are reflected from the object. For example, in ultrasonic fingerprint imagers, an ultrasonic pulse may be produced by starting and stopping the transmitter during a very short interval of time. At each material interface encountered by the ultrasonic pulse, a portion of the ultrasonic pulse may be reflected.

For example, in the context of an ultrasonic fingerprint imager, the ultrasonic wave may travel through a platen on which a person's finger may be placed to obtain a fingerprint image. After passing through the platen, some portions of the ultrasonic wave encounter skin that is in contact with the platen, e.g., fingerprint ridges, while other portions of the ultrasonic wave encounter air, e.g., valleys between adjacent ridges of a fingerprint, and may be reflected with different intensities back towards the ultrasonic sensor array. The reflected signals associated with the finger may be processed and converted to a digital value representing the signal strength of the reflected signal. When such reflected signals are collected over a distributed area, the digital values of such signals may be used to produce a graphical display of the signal strength over the distributed area, for example by converting the digital values to an image, thereby producing an image of the fingerprint. Thus, an ultrasonic sensor system may be used as a fingerprint imager.

BRIEF DESCRIPTION OF THE DRAWINGS

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale. Like reference numbers and designations in the various drawings indicate like elements.

FIGS. 7A and 7B show examples of ultrasonic receivers with and without spacer layers disposed between the ultrasonic receiver and a platen.

FIGS. 9A-9C show examples of ultrasonic sensors including backside protective caps.

DETAILED DESCRIPTION

Figures 1A, 1B, 1C:
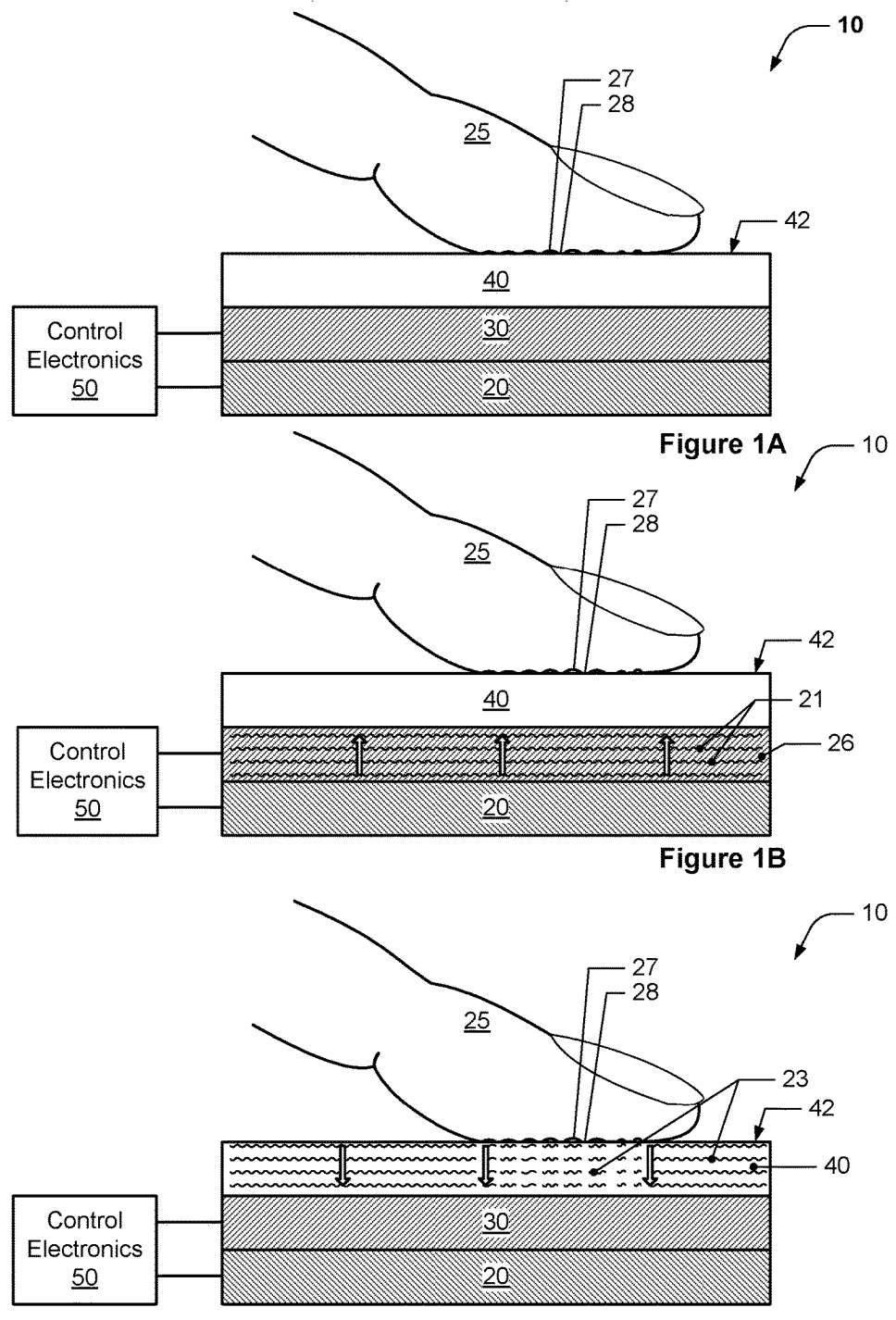
FIGS. 1A-1C show an example of a schematic diagram of an ultrasonic sensor system.

The following description is directed to certain implementations for the purposes of describing the innovative aspects of this disclosure. However, a person having ordinary skill in the art will readily recognize that the teachings herein may be applied in a multitude of different ways. The described implementations may be implemented in any device, apparatus, or system that includes an ultrasonic sensing system. In addition, it is contemplated that the described implementations may be included in or associated with a variety of electronic devices such as, but not limited to: mobile telephones, multimedia Internet enabled cellular telephones, mobile television receivers, wireless devices, smartphones, Bluetooth® devices, personal data assistants (PDAs), wireless electronic mail receivers, hand-held or portable computers, netbooks, notebooks, smartbooks, tablets, printers, copiers, scanners, facsimile devices, global positioning system (GPS) receivers/navigators, cameras, digital media players (such as MP3 players), camcorders, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, camera view displays (such as the display of a rear view camera in a vehicle), electronic photographs, electronic billboards or signs, projectors, architectural structures, microwaves, refrigerators, stereo systems, cassette recorders or players, DVD players, CD players, VCRs, radios, portable memory chips, washers, dryers, washer/dryers, parking meters, packaging (such as in electromechanical systems (EMS) applications including microelectromechanical systems (MEMS) applications, as well as non-EMS applications), aesthetic structures (such as display of images on a piece of jewelry or clothing) and a variety of EMS devices. The teachings herein also may be used in applications such as, but not limited to, electronic switching devices, radio frequency filters, sensors, accelerometers, gyroscopes, motion-sensing devices, magnetometers, inertial components for consumer electronics, parts of consumer electronics products, varactors, liquid crystal devices, electrophoretic devices, drive schemes, manufacturing processes and electronic test equipment. Thus, the teachings are not intended to be limited to the implementations depicted solely in the Figures, but instead have wide applicability as will be readily apparent to one having ordinary skill in the art.

Some implementations described herein relate to ultrasonic sensors including piezoelectric receiver layers bonded to thin film transistor (TFT) arrays with an adhesive. Some implementations relate to processes for forming ultrasonic sensors including bonding a piezoelectric receiver layer to a TFT array. Advantages of implementations described herein include ultrasonic sensors that may be implemented with standard TFT arrays. Implementations described herein allow bonding piezoelectric receiver layers without special modification to TFT processing.

FIGS. 1A-1C show an example of a schematic diagram of an ultrasonic sensor system. As shown in FIG. 1A, ultrasonic sensor system 10 includes an ultrasonic transmitter 20 and an ultrasonic receiver 30 under a platen 40. The ultrasonic transmitter 20 may be a piezoelectric transmitter that can generate ultrasonic waves 21 (see FIG. 1B). The ultrasonic receiver 30 includes a piezoelectric material and an array of pixel circuits disposed on a substrate. In operation, the ultrasonic transmitter 20 generates an ultrasonic wave 21 that travels through the ultrasonic receiver 30 to the exposed surface 42 of the platen 40. At the exposed surface 42 of the platen 40, the ultrasonic energy may be transmitted into, absorbed or scattered by an object 25 that is in contact with the platen 40, such as the skin of a fingerprint ridge 28, or reflected back. In those locations where air contacts the exposed surface 42 of the platen 40, e.g., valleys 27 between fingerprint ridges 28, most of the ultrasonic wave 21 will be reflected back toward the ultrasonic receiver 30 for detection (see FIG. 1C). Control electronics 50 may be coupled to the ultrasonic transmitter 20 and ultrasonic receiver 30 and may supply timing signals that cause the ultrasonic transmitter 20 to generate one or more ultrasonic waves 21. The control electronics 50 may then receive signals from the ultrasonic receiver 30 that are indicative of reflected ultrasonic energy 23. The control electronics 50 may use output signals received from the ultrasonic receiver 30 to construct a digital image of the object 25.

Figure 2:
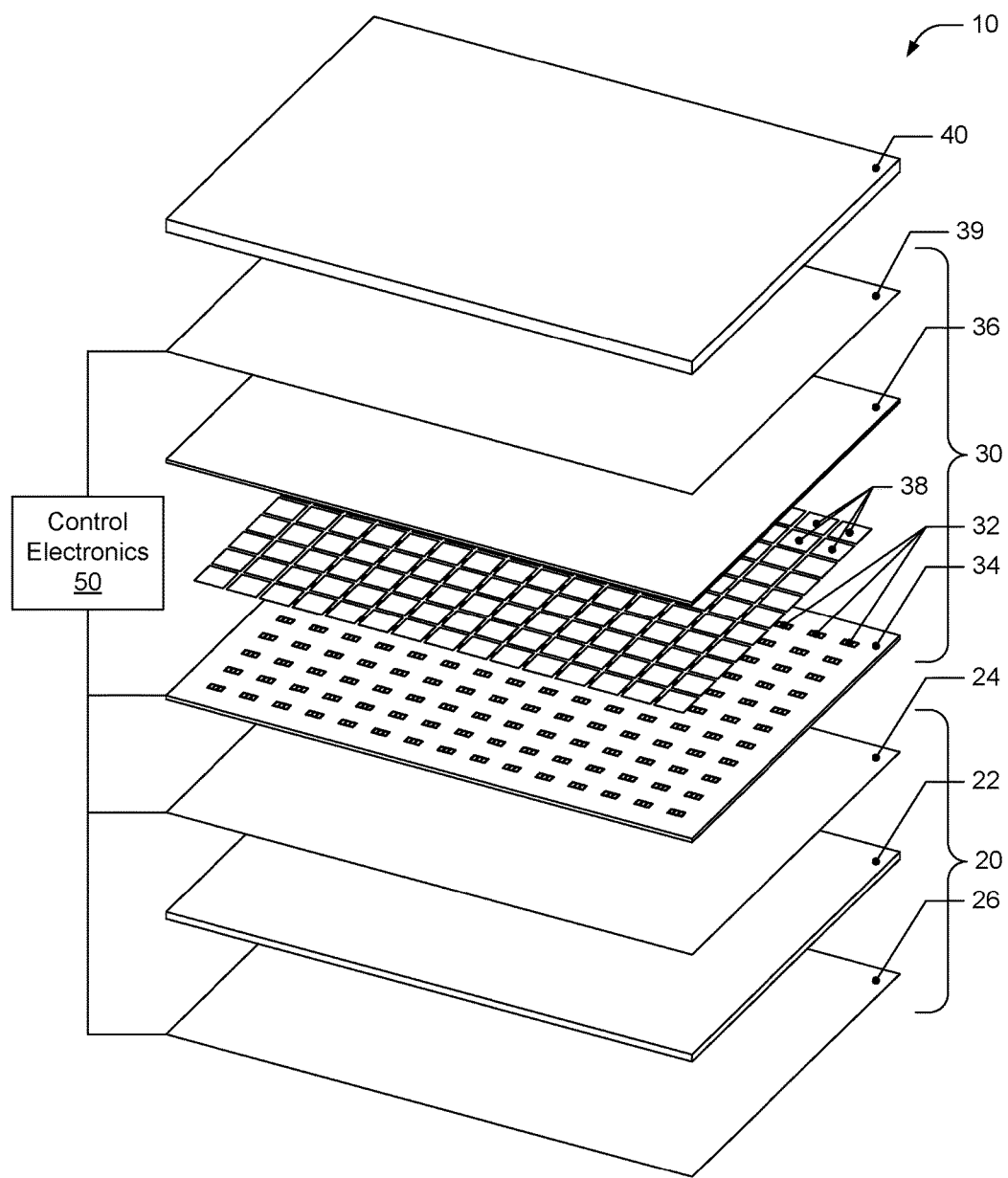
FIG. 2 shows an example of an exploded view of an ultrasonic sensor system.

FIG. 2 shows an example of an exploded view of an ultrasonic sensor system 10 including an ultrasonic transmitter 20 and an ultrasonic receiver 30 under a platen 40. The ultrasonic transmitter 20 may be a plane wave generator including a substantially planar piezoelectric transmitter layer 22. Ultrasonic waves may be generated by applying a voltage to the piezoelectric layer to expand or contract the layer, depending upon the signal applied, thereby generating a plane wave. The voltage may be applied to the piezoelectric transmitter layer 22 via a first transmitter electrode 24 and a second transmitter electrode 26. In this fashion, an ultrasonic wave may be made by expanding or contracting the piezoelectric transmitter layer 22. This ultrasonic wave may travel towards a finger (or other object to be detected), passing through the platen 40. A portion of the wave not absorbed or transmitted by the object to be detected may be reflected so as to pass back through the platen 40 and be received by the ultrasonic receiver 30. The first and second transmitter electrodes 24 and 26 may be metallized or otherwise conductive electrodes, for example, metal layers that coat opposing sides of the piezoelectric transmitter layer 22.

Figure 3A:
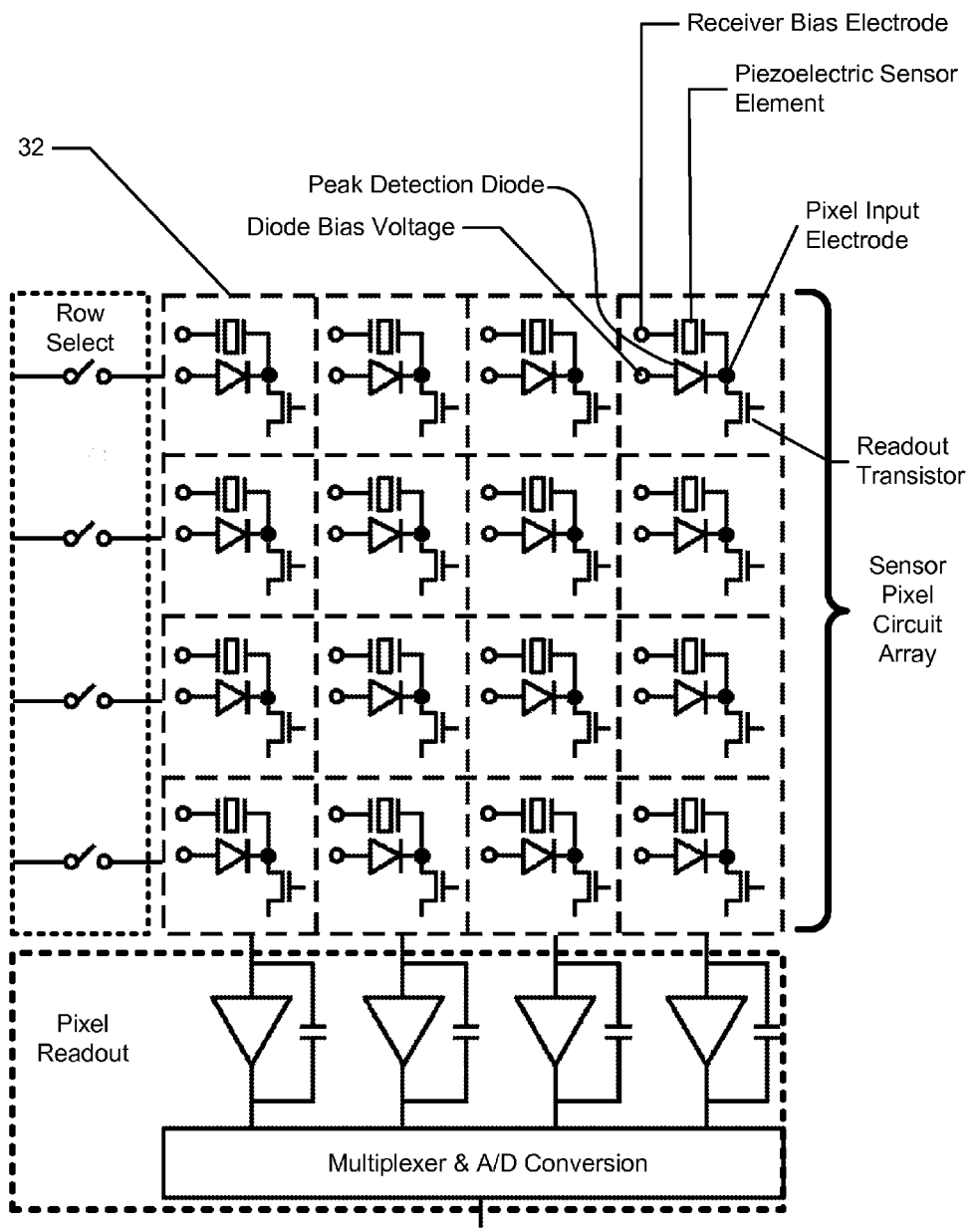
FIG. 3A shows an example of a 4×4 pixel array of pixels for an ultrasonic sensor.

The ultrasonic receiver 30 may include an array of pixel circuits 32 disposed on a substrate 34, which also may be referred to as a backplane, and a piezoelectric receiver layer 36 positioned on or otherwise coupled to the underlying pixel circuits 32. In some implementations, each pixel circuit 32 may include one or more thin-film transistors and, in some implementations, one or more additional circuit elements such as diodes, capacitors, and the like. Each pixel circuit 32 may be configured to convert an electric charge generated by the piezoelectric receiver layer 36 proximate to the pixel circuit into an electrical signal. Each pixel circuit 32 may include a pixel input electrode 38 that electrically couples the piezoelectric receiver layer 36 to the pixel circuit 32. In the illustrated implementation, a receiver bias electrode 39 is disposed on a side of the piezoelectric receiver layer 36 opposite the pixel circuits 32. The receiver bias electrode 39 may be grounded or biased to control which signals are passed to a TFT array. The receiver bias electrode may include, for example, one or more layers of aluminum, an aluminum alloy, copper, a copper alloy, copper and nickel, gold, platinum and gold, chrome and gold, chrome and aluminum, chrome and copper, chrome with copper and gold, silver, indium-tin-oxide (ITO) or other conductive oxide, silver and urethane polymer, or other suitably conductive material. Ultrasonic energy that is reflected from the exposed (top) surface of the platen 40 is converted into localized electrical charges by the piezoelectric receiver layer 36. These localized charges may be collected by the pixel input electrodes 38 and passed on to the underlying pixel circuits 32. The charges may be amplified by the pixel circuits 32 and output signals from the pixel circuits may be sent to a sensor controller or other circuitry for signal processing. A simplified schematic of an example pixel circuit 32 is shown in FIG. 3A, however one of ordinary skill in the art will appreciate that many variations of and modifications to the example pixel circuit 32 shown in the simplified schematic may be contemplated.

Control electronics 50 may be electrically connected with the first transmitter electrode 24 and the second transmitter electrode 26, as well as with the receiver bias electrode 39 and the pixel circuits 32 on the TFT substrate 34. The control electronics 50 may operate substantially as discussed previously with respect to FIGS. 1A-1C.

The platen 40 can be any appropriate material that can be acoustically coupled to the receiver, with examples including plastic, ceramic, sapphire, composite materials, metal and metal alloys, metal-filled polymers, polycarbonate, and glass. In some implementations, the platen 40 can be a cover plate, e.g., a cover glass or a cover lens for a display. In some implementations, the platen 40 may be a metal such as aluminum, an aluminum alloy, chrome-molybdenum, stainless steel, or a metal-filled polymer. Detection and imaging can be performed through relatively thick platens if desired, e.g., 1 mm or more. In some implementations, a casing or housing for an electronic device may serve as a platen. In some implementations, the back, sides or front of a mobile device enclosure may serve as a platen, as the ultrasonic sensor described herein may image fingerprints or acquire biometric information directly through the enclosure wall. In some implementations, a coating such as a thin layer of urethane, acrylic, parylene or a diamond-like coating (DLC) may serve as a platen.

Examples of piezoelectric materials that may be employed according to various implementations include piezoelectric polymers having appropriate acoustic properties, for example, an acoustic impedance between about 2.5 MRayls and 5 MRayls. Specific examples of piezoelectric materials that may be employed include ferroelectric polymers such as polyvinylidene fluoride (PVDF) and polyvinylidene fluoride-trifluoroethylene (PVDF-TrFE) copolymers. Examples of PVDF copolymers include 60:40 (molar percent) PVDF-TrFE, 70:30 PVDF-TrFE, 80:20 PVDF-TrFE, and 90:10 PVDR-TrFE. Other examples of piezoelectric materials that may be employed include Teflon® and other PTFE polymers, polyvinylidene chloride (PVDC) homopolymers and copolymers, polytetrafluoroethylene (PTFE) homopolymers and copolymers, and diisopropylammonium bromide (DIPAB).

The thickness of each of the piezoelectric transmitter layer 22 and the piezoelectric receiver layer 36 may be selected so as to be suitable for generating and receiving ultrasonic waves. In one example, a PVDF piezoelectric transmitter layer 22 is approximately 28 μm thick and a PVDF-TrFE receiver layer 36 is approximately 12 μm thick. Example frequencies of the ultrasonic waves are in the range of 5 MHz to 30 MHz, with wavelengths on the order of a quarter of a millimeter or less.

FIGS. 1A through 1C and 2 show example arrangements of ultrasonic transmitters and receivers in an ultrasonic sensor system, with other arrangements possible. For example, in some implementations, the ultrasonic sensor system may include an acoustic delay layer. For example, an acoustic delay layer can be incorporated into the ultrasonic sensor system 10 between the ultrasonic transmitter 20 and the ultrasonic receiver 30. An acoustic delay layer can be employed to adjust the ultrasonic pulse timing, and at the same time electrically insulate the ultrasonic receiver 30 from the ultrasonic transmitter 20. The delay layer may have a substantially uniform thickness, with the material used for the delay layer and/or the thickness of the delay layer selected to provide a desired delay in the time for reflected ultrasonic energy to reach the ultrasonic receiver 30. In doing so, the range of time during which an energy pulse that carries information about the object by virtue of having been reflected by the object may be made to arrive at the ultrasonic receiver 30 during a time range when it is unlikely that energy reflected from other parts of the ultrasonic sensor system 10 is arriving at the ultrasonic receiver 30. In some implementations, the TFT substrate 34 and/or the platen 40 may serve as an acoustic delay layer.

FIG. 3A depicts a 4×4 pixel array of pixels for an ultrasonic sensor. Each pixel may, for example, be associated with a local region of piezoelectric sensor material, a peak detection diode and a readout transistor; many or all of these elements may be formed on or in the backplane to form the pixel circuit. In practice, the local region of piezoelectric sensor material of each pixel may transduce received ultrasonic energy into electrical charges. The peak detection diode may register the maximum amount of charge detected by the local region of piezoelectric sensor material. Each row of the pixel array may then be scanned, e.g., through a row select mechanism, a gate driver, or a shift register, and the readout transistor for each column may be triggered to allow the magnitude of the peak charge for each pixel to be read by additional circuitry, e.g., a multiplexer and an A/D converter. The pixel circuit may include one or more TFTs to allow gating, addressing, and resetting of the pixel.

Each pixel circuit 32 may provide information about a small portion of the object detected by the ultrasonic sensor system 10. While, for convenience of illustration, the example shown in FIG. 3A is of a relatively coarse resolution, ultrasonic sensor systems having a resolution on the order of 500 pixels per inch or higher that are configured with a layered structure substantially similar to that shown in FIG. 2 have been demonstrated by the present inventors. The detection area of the ultrasonic sensor system 10 may be selected depending on the intended object of detection. For example, the detection area may range from 5 mm×5 mm for a single finger to 3 inches×3 inches for four fingers. Smaller and larger areas may be used as appropriate for the object.

Figure 3B:
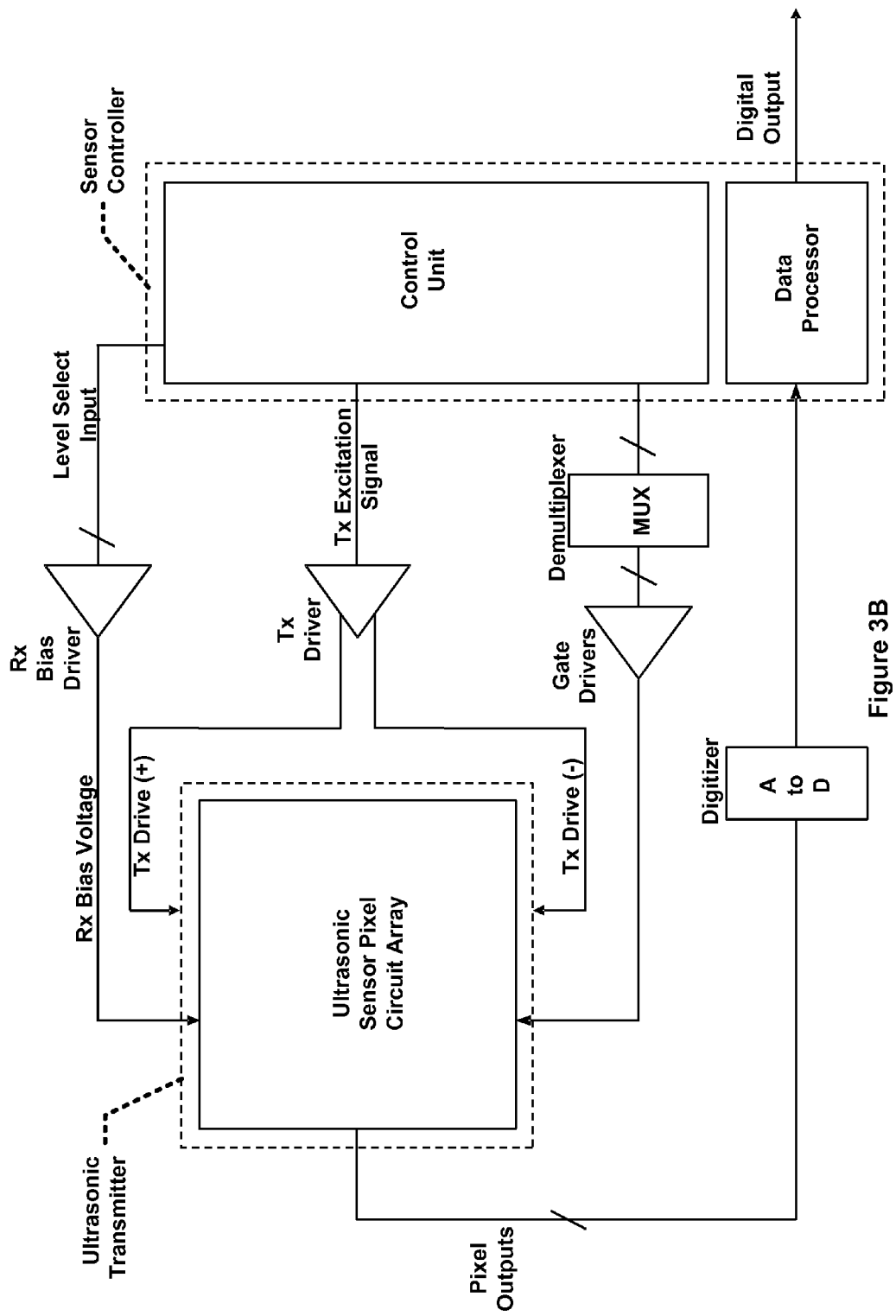
FIG. 3B shows an example of a high-level block diagram of an ultrasonic sensor system.

FIG. 3B shows an example of a high-level block diagram of an ultrasonic sensor system. Many of the elements shown may form part of control electronics 50. A sensor controller may include a control unit that is configured to control various aspects of the sensor system, e.g., ultrasonic transmitter timing and excitation waveforms, bias voltages for the ultrasonic receiver and pixel circuitry, pixel addressing, signal filtering and conversion, readout frame rates, and so forth. The sensor controller may also include a data processor that receives data from the ultrasonic sensor circuit pixel array. The data processor may translate the digitized data into image data of a fingerprint or format the data for further processing.

For example, the control unit may send a transmitter (Tx) excitation signal to a Tx driver at regular intervals to cause the Tx driver to excite the ultrasonic transmitter and produce planar ultrasonic waves. The control unit may send level select input signals through a receiver (Rx) bias driver to bias the receiver bias electrode and allow gating of acoustic signal detection by the pixel circuitry. A demultiplexer may be used to turn on and off gate drivers that cause a particular row or column of sensor pixel circuits to provide output signals. Output signals from the pixels may be sent through a charge amplifier, a filter such as an RC filter or an anti-aliasing filter, and a digitizer to the data processor. Note that portions of the system may be included on the TFT backplane and other portions may be included in an associated integrated circuit.

As indicated above, some implementations described herein relate to ultrasonic receivers including piezoelectric receiver layers bonded to TFT arrays with an adhesive. Some implementations relate to processes for forming ultrasonic sensors include bonding a piezoelectric receiver layer to a TFT array.

As used herein "bonding" refers to the fastening together of two or more solid objects by the use of glue, cement, or other adhesive, and "bonded" to the two or more solid objects so fastened. Examples of adhesives include one- and two-part epoxies, cyanoacrylates, silicones, polyurethane, thermoplastics, elastomeric adhesives, thermoset adhesives, UV-curable adhesives, hot curing adhesives, hot-melt adhesives, phenolics, acrylics, acrylates, polyamides, contact adhesives and pressure sensitive adhesives (PSAs).

Some implementations described herein relate to ultrasonic fingerprint imagers. As used herein, the term "fingerprint" may refer to a fingerprint or a thumbprint.

Figure 4:
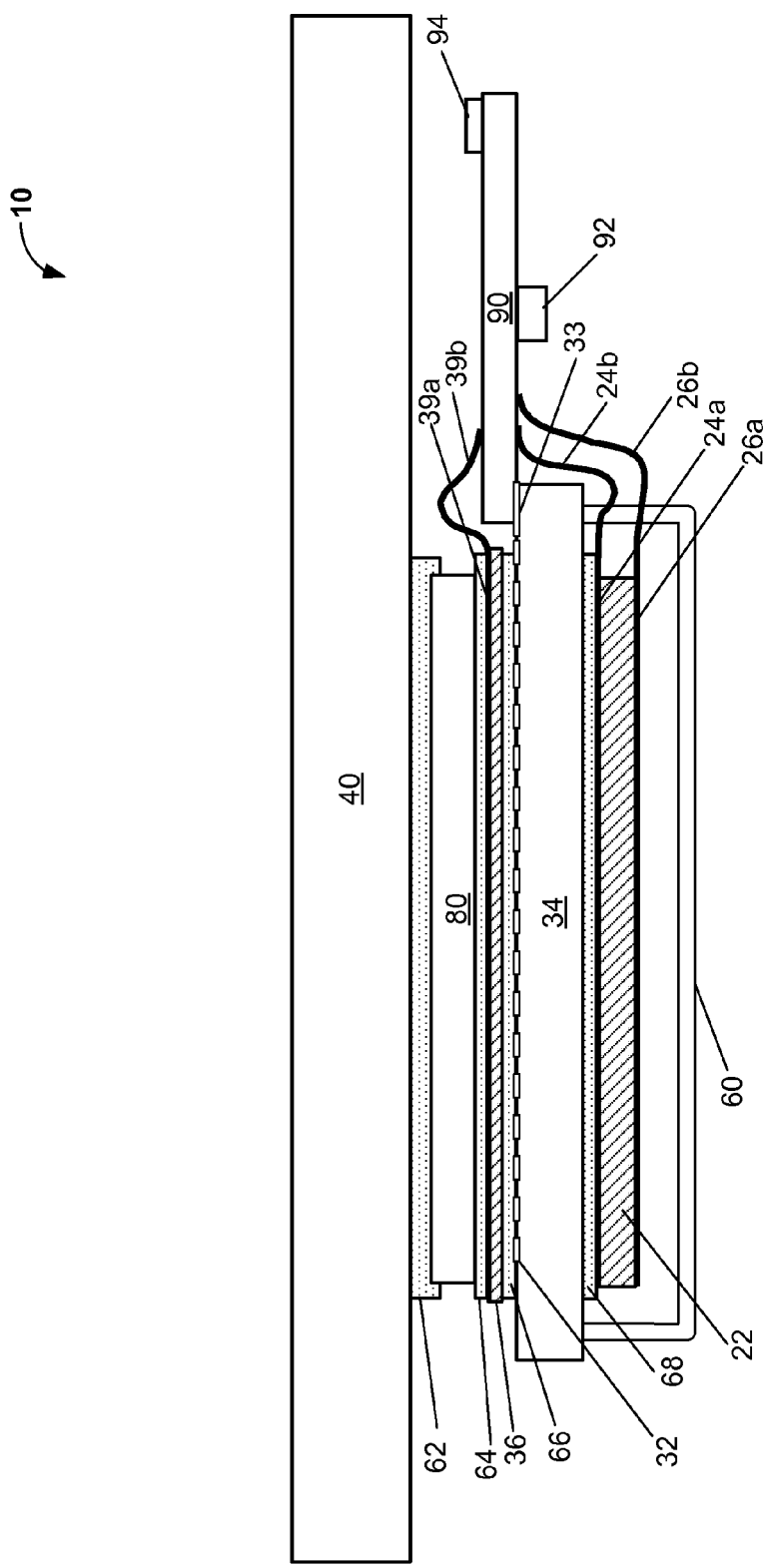
FIG. 4 shows an example of a schematic diagram of an ultrasonic sensor system including a bonded piezoelectric receiver layer.

FIG. 4 shows an example of a schematic diagram of an ultrasonic sensor system 10 including a bonded piezoelectric receiver layer 36. A brief description of various components of an ultrasonic sensor system including a bonded piezoelectric layer is given with respect to FIG. 4, with details of the components and further examples of ultrasonic sensor systems including bonded piezoelectric layers discussed further below with respect to FIGS. 7A-13G. The ultrasonic sensor system 10 includes a platen 40, a piezoelectric receiver layer 36, a TFT substrate 34, and a piezoelectric transmitter layer 22, as discussed above with reference to FIGS. 1 and 2.

Both sides of the piezoelectric transmitter layer 22 may be metallized or otherwise coated with a conductive material to form a first transmitter electrode 24a, which can be connected to a first transmitter lead 24b, and a second transmitter electrode 26a, which can be connected to second transmitter lead 26b. The metallized piezoelectric transmitter film may be bonded to the TFT substrate 34 by an adhesive 68. Adhesive 68 and other adhesive layers such as adhesive 62, adhesive 64, and adhesive 66 are enlarged for clarity in FIGS. 4 and 7A-12B, and like other layers in the Figures are generally not drawn to scale.

In the example of FIG. 4, a spacer layer 80 is disposed between the piezoelectric receiver layer 36 and the platen 40. The spacer layer 80 may provide clearance for various components of the ultrasonic sensor system 10, including components attached to a flexible printed circuit (FPC) 90. Flexible printed circuits may also be known simply as "flex." It is understood that the FPC 90 may include one or more electrodes or electrical conductors within the FPC 90 or on one or both sides of the FPC 90. As discussed further below, the spacer layer 80 may not be present in some implementations. If present, the spacer layer 80 may be bonded to the platen 40 via an adhesive 62 and to the metallized side of the piezoelectric receiver layer 36 with an adhesive 64.

One side of the piezoelectric receiver layer 36 may be metallized to form a receiver bias electrode 39a, which can be connected to a receiver bias electrode lead 39b. According to various implementations, the receiver bias electrode 39a and receiver bias electrode lead 39b may use the same or different materials. The other side of piezoelectric receiver layer 36 may be bonded to pixel circuits 32 by an adhesive 66. As discussed above with respect to FIG. 2, each pixel circuit 32 may include a pixel input electrode. The piezoelectric receiver layer 36 may be electrically coupled or otherwise connected to the pixel circuits 32 through the pixel input electrodes. In some implementations, the piezoelectric receiver layer 36 is capacitively coupled to the pixel circuits 32 through the adhesive 66. In some implementations, the piezoelectric receiver layer 36 is resistively coupled to the pixel circuits 32 through, for example, an anisotropically conductive or lightly conductive adhesive 66.

The TFT substrate 34 may be a thin substrate, e.g., a glass or plastic substrate, on which the pixel circuits 32 are fabricated. In some implementations, the TFT substrate 34 may be silicon, single-crystal silicon or other semiconductor material, such as a silicon wafer or a silicon-on-insulator wafer. The pixel circuits 32 and other circuitry related to TFT substrate 34 may be formed from transistors fabricated in the substrate, such as a conventional silicon device wafer. An example of pixel circuits 32 are shown in FIG. 3A, as discussed above. In addition to the pixel circuits 32, the TFT substrate may have additional components fabricated thereon, such as one or more conductive bond pads 33. In some implementations, a protective backside cap 60 may be disposed to protect the elements within such as the piezoelectric transmitter layer 22 from mechanical or environmental damage. The protective cap 60 may provide protection for the elements within the cap 60 from electromagnetic interference (EMI) or devices outside the cap 60 from the EMI generated by the elements within.

The FPC 90 may have one or more passive or active components mounted thereon. The first transmitter lead 24b, the second transmitter lead 26b, and the receiver bias electrode lead 39b may be configured to be in electrical communication with one or more of these components via the FPC 90. For example, a chip-on-flex (COF)-attached application specific integrated circuit (ASIC) 92 may be disposed on one side or the other of the FPC 90. One or more discrete devices such as capacitors, resistors and inductors may be included on one or both sides of FPC 90 (not shown). The ultrasonic sensor system 10 may further be configured to connect to a printed circuit board (PCB) or other integration substrate via the FPC 90. In some implementations, one or more stiffeners 94 may be attached to the FPC 90. Examples of materials for the leads include conductive inks, copper films, and other conductors. In some implementations, wire bonds or braided wire may be employed. Examples of stiffener materials include both conductive and insulative materials such aluminum, anodized aluminum, stainless steel, printed-circuit board material such as FR4, polyimide materials, and thermoplastics.

Figure 5:
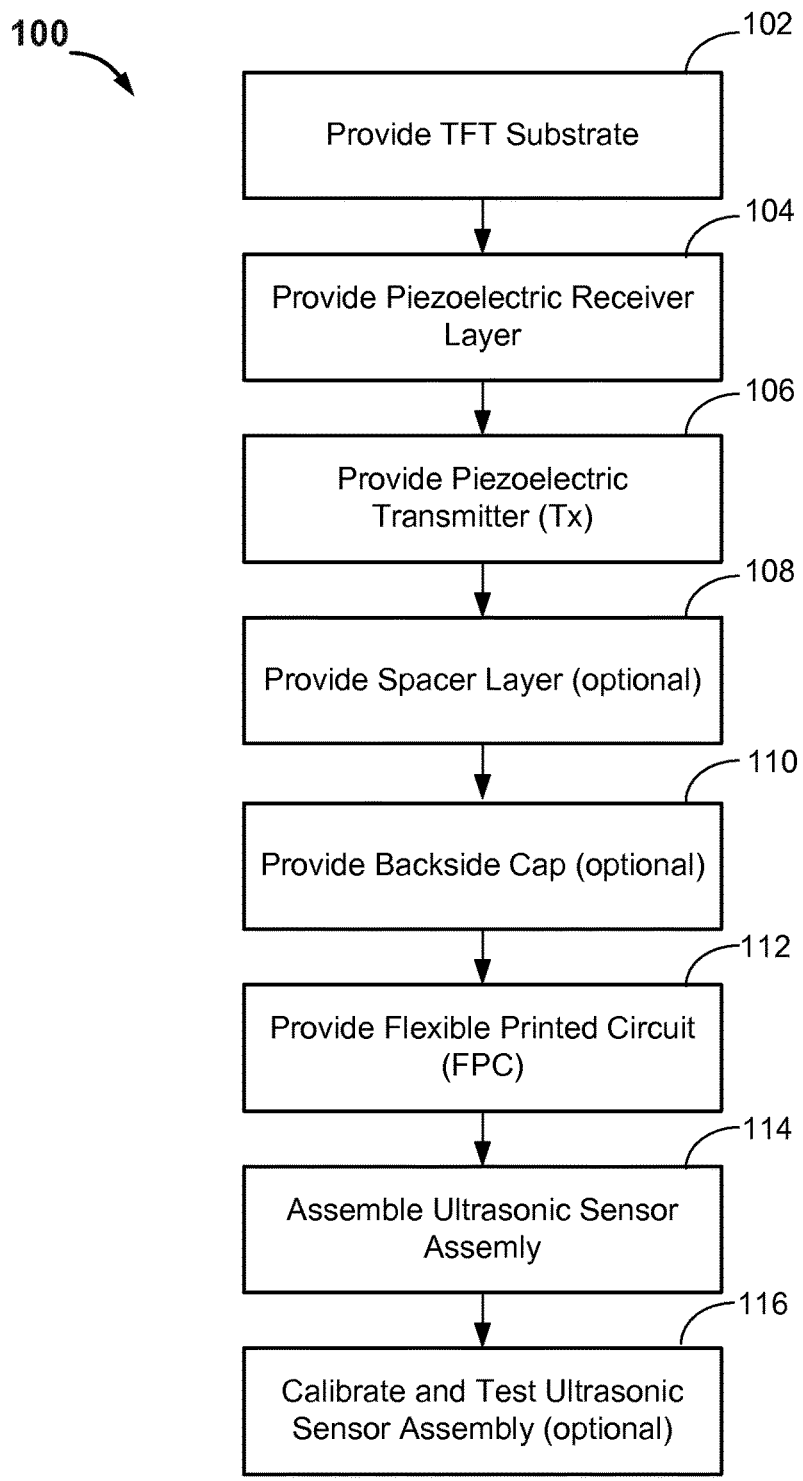
FIGS. 5 and 6 are examples of flow diagrams illustrating manufacturing processes for an ultrasonic sensor.

FIG. 5 is an example of a flow diagram illustrating a manufacturing process for an ultrasonic sensor. At block 102 of the manufacturing process 100, a TFT substrate is provided. The TFT substrate may include pixel circuits formed thereon including conductive pads deposited over the inputs of the pixel circuits to form pixel input electrodes. As indicated above, the TFT substrate may also include conductive routing and bond pads to provide connections between the pixel circuits, the ultrasonic receiver, the ultrasonic transmitter, a flexible printed circuit, or other electrical components according to the particular implementation. Standard TFT processing may be employed to form the TFT substrate. In some implementations, the TFT substrate may include a borosilicate glass with a thickness between about 300 and 700 microns. In some implementations, the glass may be thinned to reduce the overall thickness of the sensor system 10. In some implementations, the TFT substrate 34 may include a thin, flexible glass or plastic layer with a thickness less than about 300 microns or less than about 100 microns. Examples of TFT substrate materials include borosilicate glass and flexible polymeric substrates including polyimide including Neopulim™ transparent polyimide, polyethylene terephthalate (PET), and polyethylene napthalate (PEN).

At block 104 of the process 100, a piezoelectric receiver layer is provided. In some implementations, the piezoelectric receiver may be provided as piezoelectric layer having single-sided metallization. At block 106, a piezoelectric transmitter (Tx) is provided. In some implementations, the piezoelectric transmitter may be provided as a piezoelectric layer having single-sided or double-sided metallization.

Examples of metallization for either the receiver or transmitter electrode layers include aluminum (Al), an aluminum alloy, copper (Cu), a copper alloy, nickel-copper (NiCu), gold (Au), platinum-gold (PtAu), chrome-gold (CrAu), chrome-aluminum (CrAl), chrome-copper (CrCu), chrome with copper and gold, silver, ITO or other conductive oxide, and silver (Ag) in a polymer matrix such as silver ink, silver epoxy, or polyurethane (AgUr). For example, one or more receiver or transmitter electrode layers may be formed from a layer of nickel or chrome between approximately 15 nm and 50 nm thick that is deposited on top of a layer of copper or copper alloy with a thickness between approximately 0.1 µm and 0.5 µm. A protective coating such as a thin layer of urethane, acrylic, parylene or a diamond-like coating (DLC) may be disposed over the metallization to provide scratch and corrosion resistance.

In some implementations, a single piezoelectric layer may be provided for both the receiver and the transmitter in wrap-around configurations. Examples of such implementations are discussed below with respect to FIGS. 12A-13G.

Blocks 108 and 110 may be optionally performed according to the particular implementation. At block 108, a spacer layer may be provided. Example spacer materials include glass substrates such as borosilicate glass, soda lime glass, and Gorilla™ glass, and plastic substrates such as polycarbonate. Example thicknesses of a spacer layer can range from about 0.1 mm to 1 mm or more. At block 110, a backside protective cap may be provided. The backside cap can be a material such as metal-coated plastic or a tin-plated steel. Example thicknesses can range from about 50 μm to 200 μm or larger.

At block 112, one or more FPCs or other electrically connective means may be provided. As indicated above, the FPC may have one or more electrical and/or mechanical components attached thereto such as ASICs, resistors, capacitors, and mechanical stiffeners.

The above-described components may be assembled at block 114 to form an ultrasonic sensor assembly Examples of assembly according to various implementations are discussed further below with respect to FIGS. 6-13G. The sensor assembly can then optionally be calibrated and tested at block 116 prior to bonding to a cover glass or other platen. In some implementations, a thin coating such as a layer of urethane, an acrylic coating, parylene, or a DLC may be applied to the outer surface of the piezoelectric receiver layer to serve as a platen and to provide scratch resistance and environmental protection.

Figure 6:
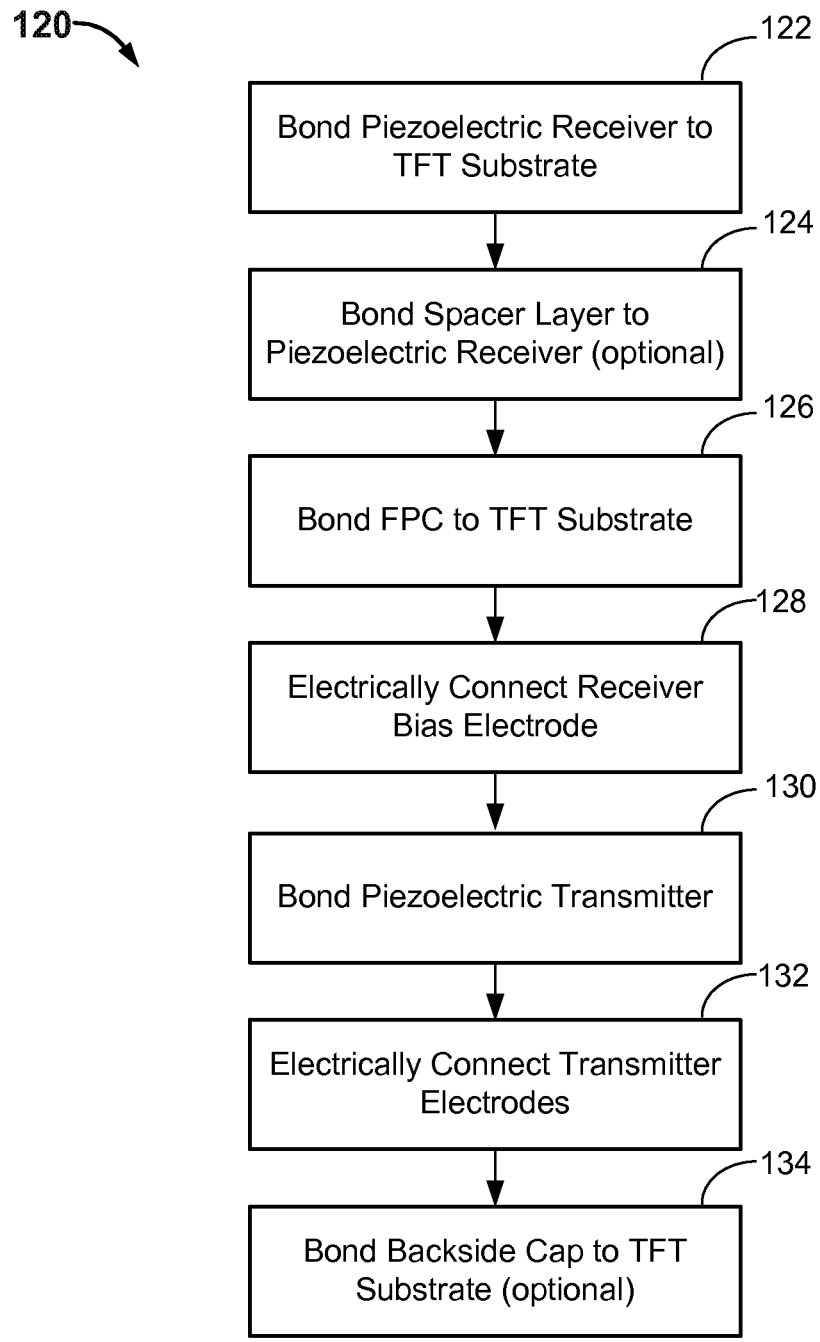

FIG. 6 is another example of a flow diagram illustrating a manufacturing process for an ultrasonic sensor. One or more operations in FIG. 6 may be performed as part of block 114 of the method 100 described above. At block 122 of the process 120, a piezoelectric receiver layer is bonded to a TFT substrate with an adhesive. As discussed further below, the adhesive may be relatively thin with a substantially uniform thickness. Bonding the piezoelectric receiver layer can include any appropriate bonding process such as vacuum bonding, hot-roll lamination, cold-roll lamination, contact bonding, hot-press bonding, cold-press bonding, or other adhesive bonding process. Examples of liquid adhesive application processes include dispensing, micro-dispensing, screen printing, silk-screening, stamping, gravure printing, slot coating, slot die coating, spraying, brushing, dipping, roller or reverse roller application, blade over drum application, wire rod application, and application by inkjet or dip pen. The adhesive is selected and bonding performed to avoid acoustic non-uniformities such as air bubbles or large variations in material density, speed of sound, and thickness. Microscopic voids, striations, local delaminations, puckers, blisters, remnant solvents, embedded particles, and material inhomogeneities are to be avoided or mitigated. Examples of adhesives may include PSAs and epoxies. In some implementations, a solvent-based adhesive may be used, where the solvent is substantially exhumed prior to making contact between joined surfaces. Joining processes may include laminating, mounting, or mating.

In some implementations, the adhesive is electrically conductive through its thickness but resistive in the lateral direction. Examples of such adhesives include anisotropic conductive film (ACF). In some implementations, a thin yet moderately resistive adhesive such as (3-aminopropyl) triethoxysilane (APTES) may be used. Employing such an adhesive may reduce or eliminate capacitive coupling between the piezoelectric receiver layer and the TFT pixel circuits. In general, adhesive bonding of the piezoelectric receiver layer to the TFT substrate is chosen to be highly electrically resistive in the lateral direction so as to avoid electrical shorting between adjacent pixel circuits and to maintain the addressability of the TFT pixel. For example, the adhesive may have a bulk or volume resistivity of more than about 1 MΩ-cm. In some implementations, a resistivity of 1E12 Ω-cm or higher may be used.

Electrically conductive transparent adhesives can be made from formulations of polyfunctional adhesion promoters, chosen such that the functional group chemistry is suitable for a given pair of bonding surfaces. One example of a suitable material for use as an electrically conductive transparent adhesive in such implementations is APTES, although other materials may also be used. APTES is a liquid at standard temperature and pressure (STP), and may be dissolved in water or acetone in a ratio of about 1 to 50% APTES by volume. In some implementations, the ratio may be about 4% APTES by volume, but ratios larger or smaller than 4% may also be used. A layer of APTES may be applied to a surface via any suitable process, including dip coating, spin coating, spray coating, or other dispensing method. In some implementations, vapor or vacuum deposition methods may be used. Prior to the application of APTES, surfaces may be cleaned and activated to improve bonding, such as oxygen plasma or ultraviolet ozone (UVO) exposure. Adjacent surfaces may be bonded to one another by applying pressure, and the bonding process may be accelerated through the application of heat during the bonding process. For example, methods such as hot pressing, hot-roll lamination, or clamping within an oven may be used to provide both pressure and heat. In some implementations, application of pressure at a temperature of about 80° C. for two hours or more provides sufficient adhesive strength, while at least 24 hours may be used at room temperature (about 25° C.). It should be noted that according to various implementations, block 122 may be performed without modification to standard TFT processing. For example, the bonding may be performed without shorting or otherwise damaging the pixel circuits.

At block 124, a spacer layer is optionally bonded to the piezoelectric receiver. Referring to FIG. 4, for example, the spacer layer 80 may serve as a standoff that ensures that the receiver bias electrode lead 39b and the FPC 90 do not interfere with mounting the TFT substrate 34 with the piezoelectric receiver layer 36 on the platen 40. The spacer layer 80 may also serve as an acoustic delay layer that improves sensor performance. FIGS. 7A and 7B, described further below, show examples of implementations with and without spacer layers. If employed, a spacer layer may be bonded with an adhesive. As discussed further below, the adhesive may be relatively thin with a uniform thickness and bonding performed in a manner to avoid acoustic non-uniformities such as air bubbles or large variations in material density or speed of sound. Examples of adhesives may include pressure sensitive adhesives, epoxies and other suitable adhesives as described above.

At block 126, an FPC is optionally bonded to the TFT substrate. One or more electrodes on the FPC can be connected to one or more conductive pads on the TFT substrate with an electrically conductive adhesive such as ACF. In some implementations discussed further below with respect to FIGS. 12A-13G, an FPC can be bonded to one or both of the piezoelectric receiver and the piezoelectric transmitter. To reduce the possibility of overheating and de-poling the piezoelectric receiver layer 36 while bonding the FPC 90 with ACF, a cooling apparatus such as a Peltier cooler, a refrigerated block cooler, or a suitably large heat sink may be thermally coupled to the piezoelectric receiver layer 36, particularly over the TFT pixel circuits 32. While applying heat to bond the FPC 90 to the TFT substrate 34 with ACF, the piezoelectric receiver layer 36 (and possibly the piezoelectric transmitter if already attached) may be cooled and retained at a temperature below the Curie temperature of the piezoelectric material.

One or more FPCs may be bonded to the ultrasonic sensor assembly, such as an FPC for the piezoelectric transmitter, an FPC for the piezoelectric receiver, one or more FPCs for the data and control lines on the TFT substrate, and combinations thereof (e.g. a data flex for transferring data and control signals, and a power flex for transferring power to the piezoelectric transmitter and receiver). The FPC may contain wider traces for supplying power to the piezoelectric transmitter or receiver, to minimize ohmic losses along the traces. The FPC may have traces and pads that connect to or mate with electrical connectors at one or both ends of the FPC. More than one connector may be included at either end. The FPC may have one or more layers of metal, such as on the topside, bottom side and internal to the flex, which may be used for carrying electrical signals. The FPC may have vias that allow electrical connections between one or more layers of the FPC. The FPC may have a multiplicity of vias to further reduce ohmic losses to the piezoelectric receiver or transmitter by connecting traces on different layers in parallel. The FPC may contain slots or cutout regions (e.g. a split flex) to allow one portion of the flex to be attached to an upper surface of a sensor assembly and another portion to a lower surface of the sensor assembly, such as to a piezoelectric receiver layer on the top side of a TFT substrate and a piezoelectric transmitter on the bottom side of the TFT substrate. The FPC may contain slots or cutout regions to allow a portion of the flex to be connected to a first connector at one end of the flex and another portion to be connected to a second connector at the same end, for example, to allow electrical connections with an external printed circuit board. The FPC may include pads for the attachment of one or more integrated circuits, capacitors, resistors, inductors, or other active or passive components. In some implementations, portions of the flex may be wrapped, folded, rolled, or otherwise bent to accommodate connections to the ultrasonic sensor assembly.

Figure 10A:
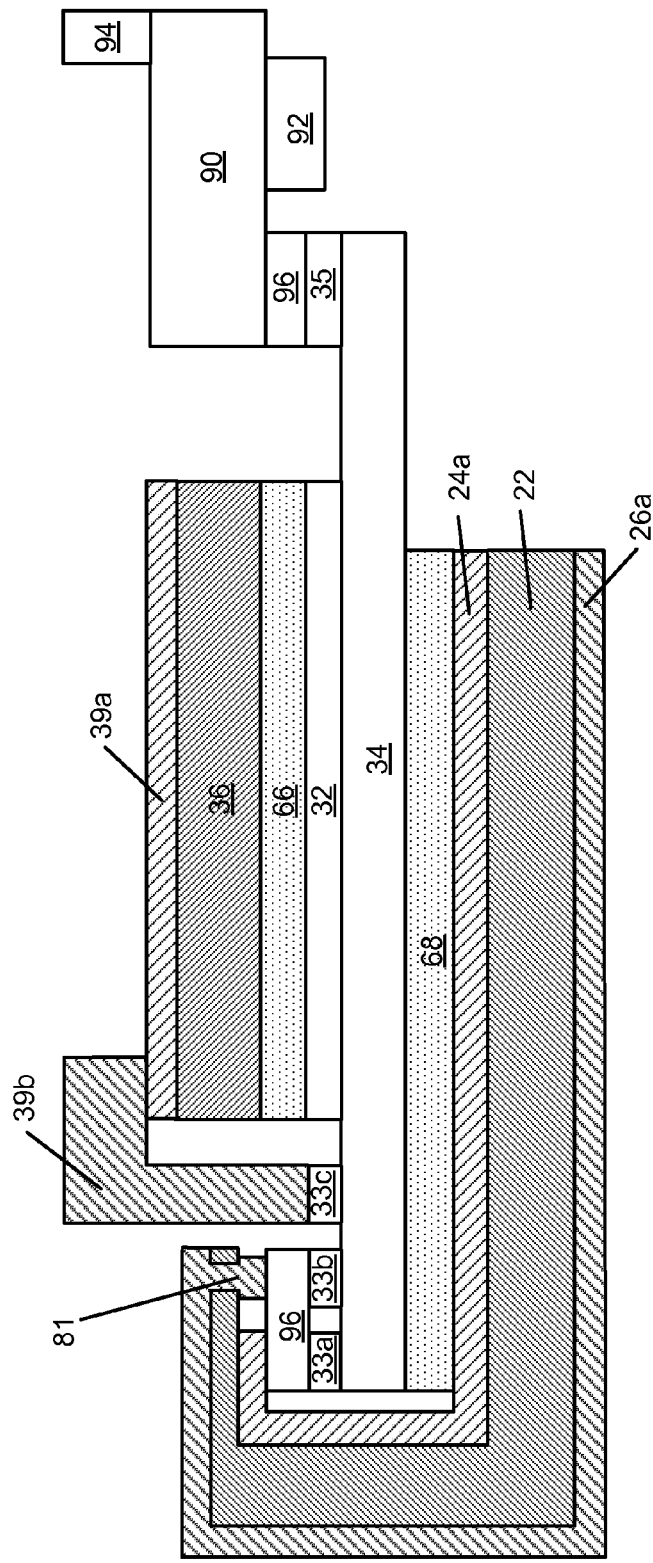
FIGS. 10A-10C show examples of electrical connections of transmitter and receiver electrodes.
Figure 10B:
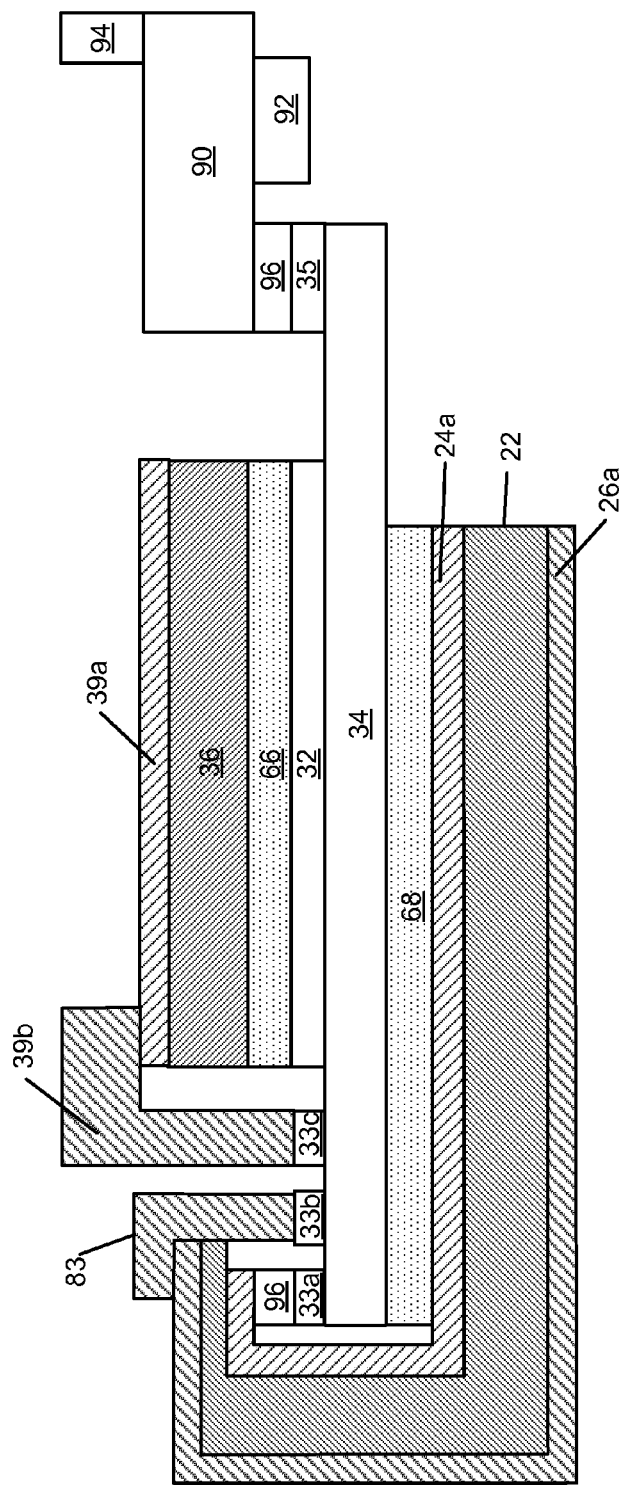
Figure 10C:
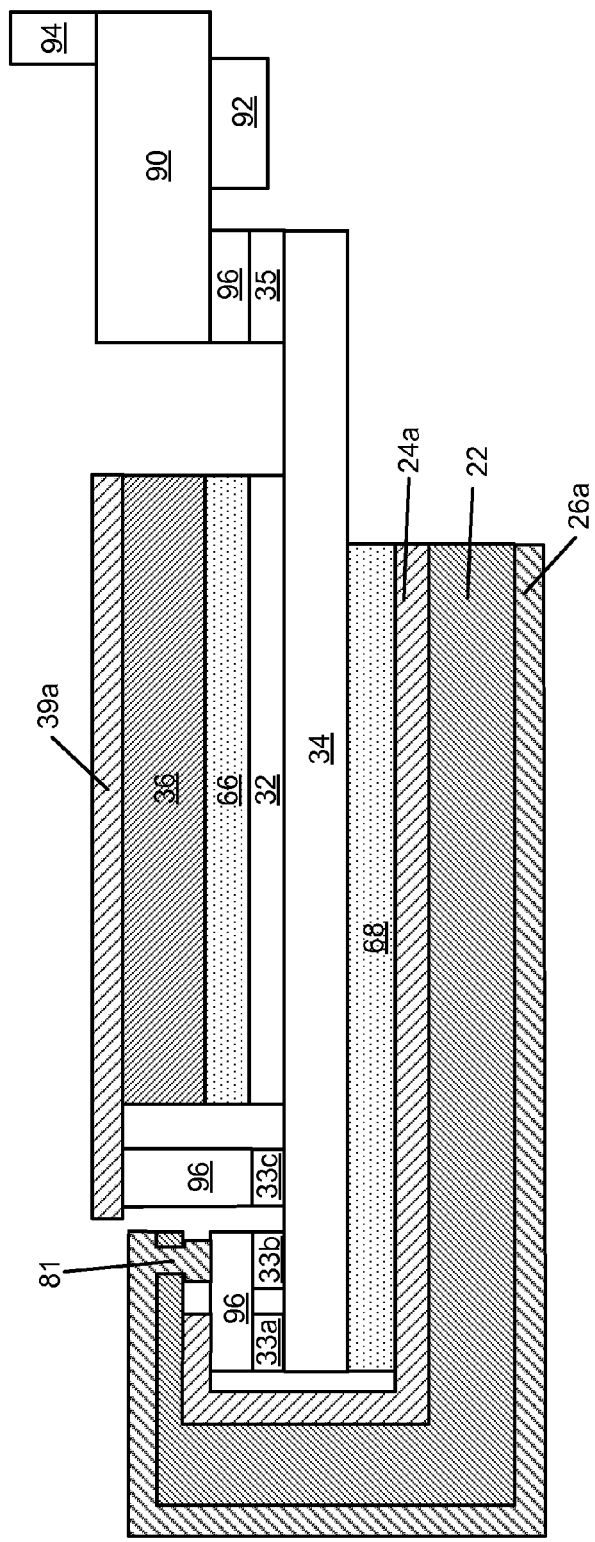
Figure 11A:
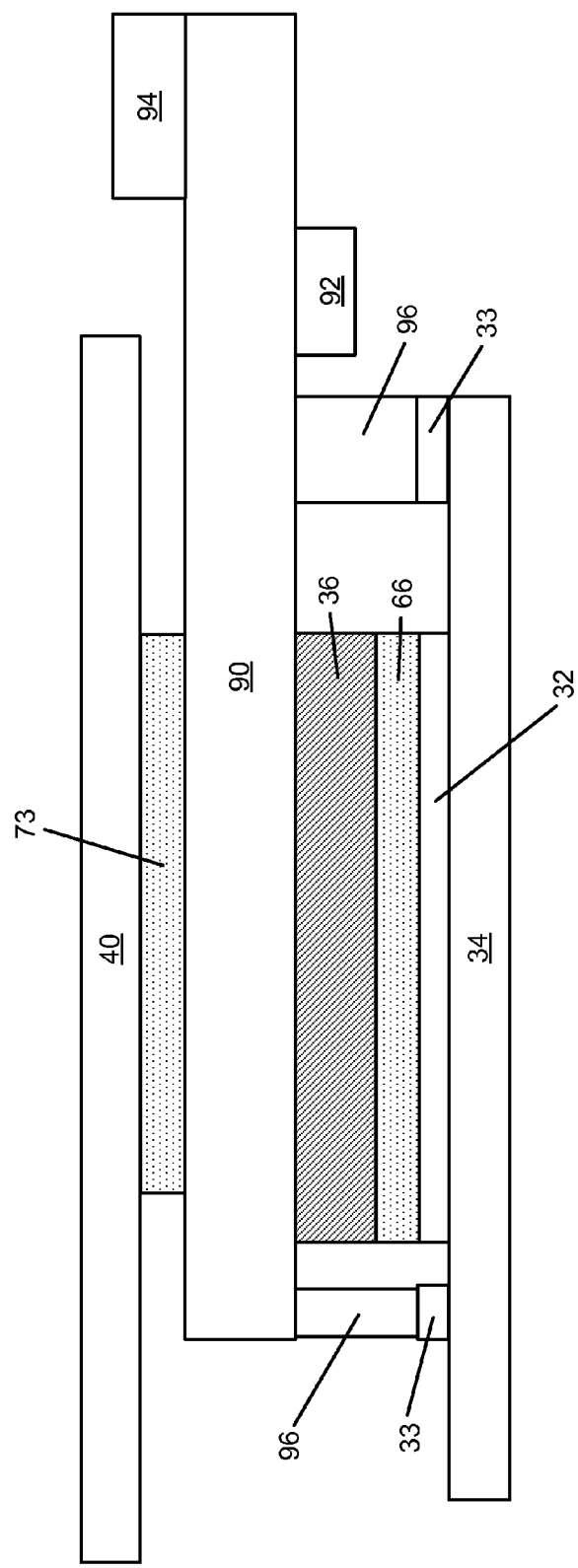
FIGS. 11A and 11B show examples of implementations in which an electrode of a flexible printed circuit is in direct electrical communication with a piezoelectric layer of an ultrasonic sensor.

At block 128, the receiver bias electrode is electrically connected. According to various implementations, the receiver bias electrode may be connected directly to the FPC or to a conductive pad on the TFT substrate for connection to the FPC. In the latter implementation, block 128 may be performed prior to block 126. Examples of materials to connect the receiver bias electrode include conductive inks, conductive epoxies, ink-jetted metal and conductive adhesives. In some implementations, the FPC may overlay or underlay the TFT substrate, in conjunction with the TFT pixel circuits, and be attached to the receiver bias electrode by hot-press bonding and/or by using a separate adhesive such as ACF. In some implementations, the FPC may overlay or underlay the TFT substrate and be attached directly to the piezoelectric receiver layer by hot-press bonding and/or by using a separate adhesive. An example of such an implementation is shown in FIG. 11A. Temperatures during this attachment can be less than 85° C. in some implementations. Additional examples of receiver connections are discussed further below with respect to FIGS. 10A-10C.

At block 130, a piezoelectric transmitter is bonded. In some implementations, the piezoelectric transmitter is bonded to the backside (i.e., the side upon which there are no pixel circuits) of the TFT substrate for example, as depicted in FIG. 4. In some implementations discussed further below with respect to FIGS. 8C and 8D, the piezoelectric transmitter is bonded to the piezoelectric receiver. Adhesives as discussed above with respect to blocks 122 and 124 may be employed.

At block 132, the transmitter electrodes are electrically connected. The transmitter electrodes may be connected directly to the FPC or to conductive bond pads on the TFT substrate. Examples of materials include conductive inks, conductive epoxies, conductive adhesives, and solders. In some implementations, the FPC may underlay or overlay the TFT substrate, in conjunction with the TFT pixel circuits, and be attached to a transmitter electrode by a conductive adhesive or other bonding method that ensures good electrical conduction between the FPC and transmitter electrodes. In some implementations, the FPC may overlay or underlay the TFT substrate, in conjunction with the TFT pixel circuits, and be attached directly to the piezoelectric transmitter layer by hot-press bonding and/or by using a separate adhesive. Temperatures during this attachment can be less than 85° C. in some implementations. These and other examples of transmitter connections are discussed further below with respect to FIGS. 10A-10C and 11B.

At block 134, a backside cap is optionally bonded to the TFT substrate. As discussed further below with respect to FIGS. 9A and 9B, in some implementations, the backside cap is sized such that there is an air gap between the transmitter and the backside cap. In some implementations, the backside cap mechanically contacts or is bonded to the transmitter or other sensor component. In some implementations, portions of the sensor assembly may be potted to form the protective cap, or a cap may be molded around portions of the sensor assembly. At this stage, the ultrasonic sensor may be tested and bonded to a cover glass or other platen as desired.

While FIGS. 5 and 6 provide examples of processes for manufacturing an ultrasonic sensor, it should be understood that the operations may be performed in different orders than the particular order shown and that in some implementations, various operations may be performed in parallel. For example, in some implementations, a single ultrasonic sensor from a single TFT substrate may be assembled as a single ultrasonic sensor through all steps in the assembly sequence. Alternatively, a strip (1×n) or array (m×n) of TFT substrates may be assembled with appropriately sized and scaled piezoelectric transmitters, piezoelectric receiver layers, spacers, protective caps, adhesives and/or other sensor elements in one or more steps of manufacturing process 100 or process 120. Strips, sheets, panels or sub-panels of TFT substrates may be diced, scribed or otherwise separated at various steps in the manufacturing process prior to attaching subsequent elements of the ultrasonic sensor assembly. Steps such as dispensing, curing and other assembly process sequences may done serially, in parallel or quasi-continuously such as in a conveyor-belt manner. For example, a curing step for ACF or a conductive epoxy may transpire at the same time and temperature as a curing step for a thermally curing adhesive layer. Liners may be included on top of PSAs that may be removed immediately prior to bonding or lamination to protect the PSA from dust and other particles. In some implementations, roll-to-roll, roll-to-glass sheet, pick-and-place, or tape-and-reel processing may be used for one or more assembly steps. For example, individual piezoelectric receiver layers or transmitters may be picked and placed onto TFT substrates or vice versa, or a sheet of m×n receivers may be picked or roll laminated onto a glass sheet of m×n TFT substrates. Further, modifications to the processes shown may be implemented without departing from the scope of the disclosure. For example, it will be understood from the examples of FIGS. 7A-13G, below, that various other operations that are not depicted can be incorporated in the example processes that are schematically illustrated. For example, one or more additional operations can be performed before, after, simultaneously, or between any of the illustrated operations. Similarly, all illustrated operations may not be performed in some implementations. It should also be understood that other elements may be included and/or certain illustrated elements omitted in the schematic diagrams below.

FIGS. 7A-13G show examples of schematic diagrams of various components of an ultrasonic sensor. The examples in these Figures provide additional detail and alternative implementations to the ultrasonic sensor described above with respect to FIG. 4. FIGS. 7A and 7B show examples of ultrasonic receivers with and without spacer layers disposed between the ultrasonic receiver and a platen. In FIGS. 7A and 7B, a piezoelectric receiver layer 36 is shown bonded to a TFT substrate 34 by an adhesive 66. Although the pixel circuits 32 are shown as an intermediate layer between the TFT substrate 34 and the piezoelectric receiver layer 36, the adhesive 66 may contact the pixel input electrodes of the pixel circuits 32, as well as the surface of the TFT substrate 34 in areas between the pixel circuits 32. Also shown in FIGS. 7A and 7B are an FPC 90, having an ASIC 92 and a stiffener 94 attached thereto and electrically connected to the pixel circuits 32 by an ACF 96 bonded to a TFT array conductive bond pad 33d, and a receiver bias electrode 39a connected to a receiver bond pad 33c by a receiver bias electrode lead 39b, which may be, for example, a metal wire, a bond wire, a metal trace, or a conductive adhesive material such as silver epoxy or silver ink. The connection between the receiver bias electrode 39a and the receiver conductive bond pad 33d may be formed in one of several ways such as dispensing, stamping, metal evaporation with a shadow mask, sputtering and photolithographic masking, or ink jetting. Other conductive leads, traces and vias may be formed in a similar manner. FIG. 7A includes a spacer layer 80, bonded to the receiver bias electrode 39a by an adhesive 64 and to a platen 40 by an adhesive 62. In FIG. 7B, no spacer layer is present, with the receiver bias electrode 39a bonded directly to the platen 40 by the adhesive 64. Examples of adhesives are described further below. Examples of spacer layer thicknesses range from about 0.1 mm to about 0.5 mm; examples of adhesive thicknesses range from about 0.001 mm to about 0.25 mm. In implementations that do not employ a spacer layer, the thickness of the adhesive 64 may be at the high end of this range to provide space for components attached to the FPC 90.

In the examples of FIGS. 7A and 7B, an ultrasonic transmitter (not depicted) may be below the TFT substrate 34 as described above with respect to FIG. 4. Various aspects of the arrangements shown in FIGS. 7A and 7B may also be implemented with an ultrasonic transmitter positioned between the TFT substrate 34 and the platen 40, including the use of a spacer layer 80 disposed between the ultrasonic transmitter and the platen 40.

Figure 8A:
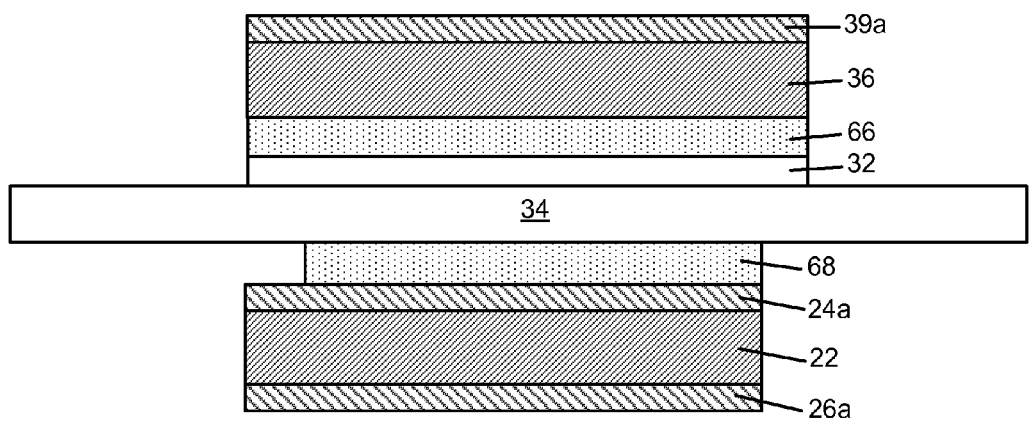
FIGS. 8A-8D show examples of arrangements of an ultrasonic transmitter and an ultrasonic receiver of an ultrasonic sensor.
Figure 8B:
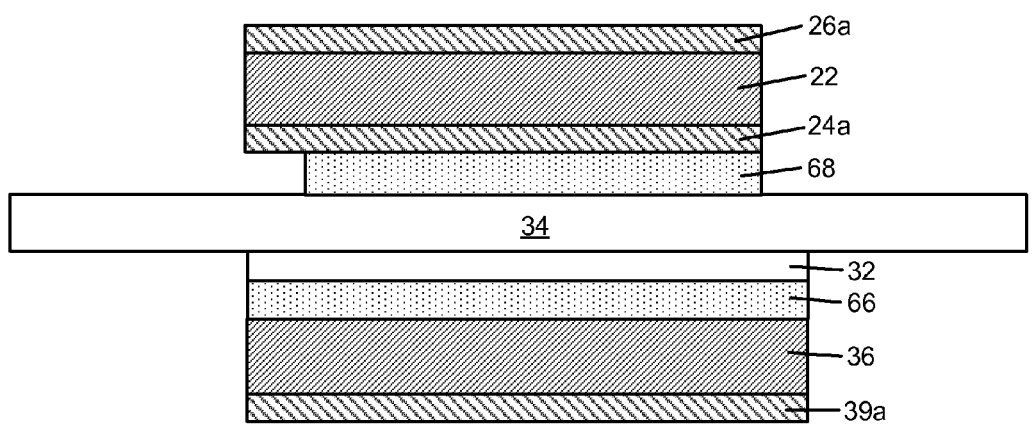

As indicated above, various placements of the ultrasonic transmitter and receiver may be employed. FIGS. 8A-8D show examples of arrangements of an ultrasonic transmitter and an ultrasonic receiver of an ultrasonic sensor. The Figures are oriented such that a platen or cover glass would be positioned above each stack. In some implementations such as that shown in FIG. 8D, the TFT substrate 34 may serve as the platen. In FIG. 8A, the ultrasonic receiver, including a piezoelectric receiver layer 36, a receiver bias electrode 39a, and pixel circuits 32, is positioned above a TFT substrate 34, with the ultrasonic transmitter, including piezoelectric transmitter layer 22 and first and second transmitter electrodes 24a and 26a, positioned below the TFT substrate 34. In FIG. 8B, the ultrasonic transmitter, including the piezoelectric transmitter layer 22 and the first and second transmitter electrodes 24a and 26a is positioned above the TFT substrate 34, with the ultrasonic receiver, including the piezoelectric receiver layer 36, the receiver bias electrode 39a, and the pixel circuits 32, positioned below the TFT substrate 34.

Figure 8C:
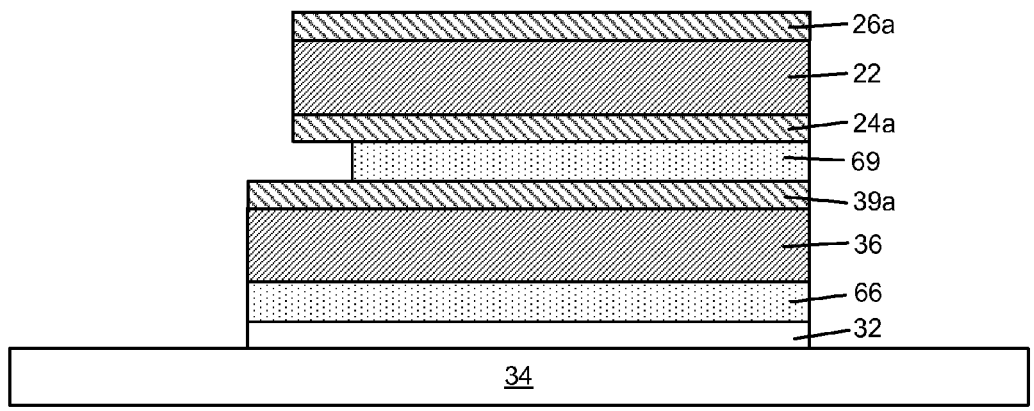

FIG. 8C shows an example of an implementation in which both the ultrasonic transmitter and the ultrasonic receiver are above the TFT substrate 34. In the example of FIG. 8C, the ultrasonic transmitter, including the piezoelectric transmitter layer 22 and the first and second transmitter electrodes 24a and 26a, is positioned above the ultrasonic receiver, with the ultrasonic transmitter bonded to the receiver bias electrode 39a of the ultrasonic receiver. The ultrasonic receiver is bonded to the TFT substrate 34, with the piezoelectric receiver layer 36 electrically coupled to the pixel circuits 32.

Figure 8D:
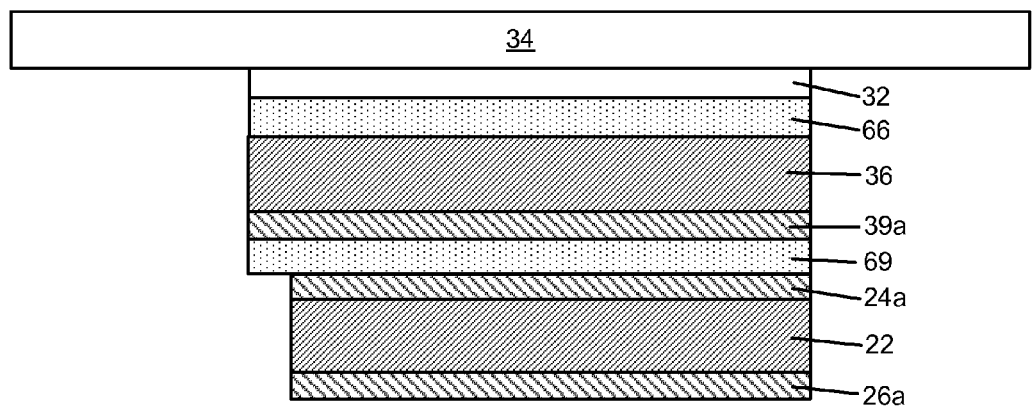

FIG. 8D shows an example of an implementation in which both the ultrasonic transmitter and the ultrasonic receiver are positioned below the TFT substrate 34. In the example of FIG. 8D, the ultrasonic transmitter, including the piezoelectric transmitter layer 22 and the first and second transmitter electrodes 24a and 26a, is positioned below the ultrasonic receiver, with the ultrasonic transmitter bonded to the receiver bias electrode 39a of the ultrasonic receiver. The ultrasonic receiver is bonded to the TFT substrate 34, with the piezoelectric receiver layer 36 electrically coupled to the pixel circuits 32. In some implementations, the side of TFT substrate 34 opposite the pixel circuits 32 may serve as the platen, and may optionally include one or more coatings. In some implementations the side of TFT substrate 34 opposite the pixel circuits 32 may be attached to a separate platen such as a cover glass, or a wall of a mobile device enclosure.

Note that in the examples of FIGS. 8A and 8B, the ultrasonic transmitter is bonded to the TFT substrate 34 with an adhesive 68, with the first transmitter electrode 24a of the ultrasonic transmitter bonded to the TFT substrate 34. In the examples of FIGS. 8C and 8D, the ultrasonic transmitter is bonded to the ultrasonic receiver with an adhesive 69, with the first transmitter electrode 24a bonded to the receiver bias electrode 39a. Examples of adhesives 68 and 69 include pressure sensitive adhesives, epoxies, and other adhesives as described above. In the examples of FIGS. 8A-8D, the piezoelectric receiver layer 36 may be bonded to the TFT substrate 34 by an adhesive 66 as described above.

As indicated above with respect to block 134 of FIG. 6, a backside cap may be optionally bonded to the TFT substrate. FIGS. 9A and 9B show examples of ultrasonic sensors including backside protective caps 60. The backside cap 60 may include a metal, a metal coating or a conductive material sufficient to reduce electromagnetic interference (EMI) and improve acoustic performance. Example thicknesses of the backside cap 60 range from about 50 μm to about 500 μm. In the example of FIG. 9A, the backside cap 60 is separated from the ultrasonic transmitter by an air gap 61. The air gap may be about 25 μm to 100 μm thick in some implementations. The air gap may provide mechanical isolation to prevent potential damage during assembly and to prevent incidental shorting of the transmitter electrode 26a. Acoustically, an air gap allows the transmitter to operate more efficiently as acoustic energy emitted from the transmitter in the backwards direction towards the backside cap is largely reflected back towards the platen or cover glass. A piezoelectric receiver layer 36 may be attached to TFT pixel circuits 32 (not shown) on TFT substrate 34 opposite the piezoelectric transmitter layer 22.

In the example of FIG. 9B, the backside cap 60 is bonded directly to the second transmitter electrode 26a by an adhesive layer 71. The backside cap 60 can also be bonded to the TFT substrate 34 by an adhesive layer 65. Examples of adhesives that can be used to bond the backside cap include pressure sensitive adhesives and epoxies having cohesive strength to provide strong, reliable adhesion to the TFT substrate 34. While the backside cap in the examples of FIGS. 9A and 9B encloses the ultrasonic transmitter and is attached to the back of the TFT substrate 34, in implementations in which the receiver is on the bottom (such as those such as those shown in FIGS. 8B and 8D), the backside cap may enclose the ultrasonic receiver and be attached to the side of the TFT substrate 34 upon which the TFT pixel circuits are located. Note that first and second transmitter leads 24b and 26b may be routed through, under, or over adhesive layer 65, or through electrically insulated passages through the backside cap 60. In some implementations, an acoustic backing layer (not shown) may be applied to the outer side of the transmitter or positioned between the transmitter and the backside cap 60. The backing layer may be made, for example, of acoustically absorptive material to absorb emitted ultrasonic energy from the backside of the transmitter and avoid undue reflections back towards the platen or cover glass. Alternatively, the backing layer may include an open-cell or closed-cell foam or foam adhesive, exhibiting a relatively small acoustic impedance relative to the piezoelectric transmitter so as to avoid undue loss of acoustic energy into the backing layer. As in FIG. 9A, a piezoelectric receiver layer 36 may be attached to TFT pixel circuits 32 (not shown) on TFT substrate 34 opposite the piezoelectric transmitter layer 22.

Figure 9C:
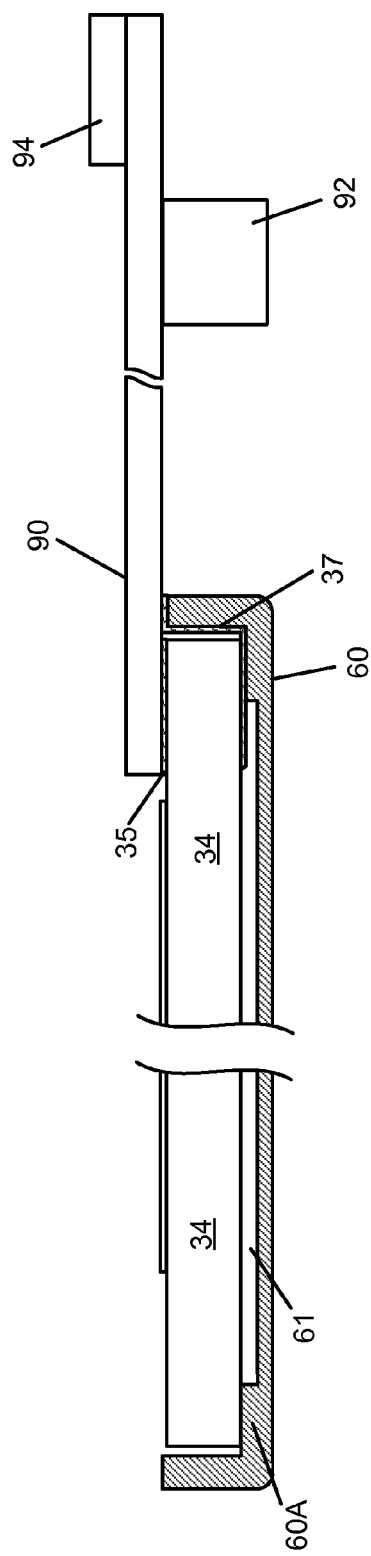

FIG. 9C shows an example in which the backside cap 60 forms a frame that snugly wraps around the TFT substrate 34. The backside cap 60 may be a molded component including a support portion 60A to support the TFT substrate 34. The support portion 60A may be or include an adhesive to the backside cap 60. One or more conductive leads 37 from an underlying transmitter and/or receiver (not shown) may be routed between the backside cap 60 and the TFT substrate 34 to an FPC 90. In some implementations, the one or more conductive leads 37 may be integrated into the backside cap 60. For example, the backside cap 60 may be metallized, e.g., with copper tape, a metal foil, or a metal coating on one or both sides of the cap. The FPC 90 may extend over the backside cap to be further connected via flex-on-glass (FOG) pads 35, which may include ACF, to electrically couple to a transmitter and/or receiver. In this manner, the transmitter and/or receiver may be connected to a COF-attached ASIC 92 disposed on the FPC 90. A stiffener 94 on the FPC 90 is also depicted in FIG. 9C.

The first and second transmitter electrodes and receiver bias electrodes may be electrically connected in various manners. As discussed above, wire bonds, conductive adhesives, and conductive inks may be used in some implementations. FIGS. 10A-10C show further examples of electrical connections of transmitter and receiver electrodes. In FIGS. 10A-10C, a piezoelectric receiver layer 36 is metallized with a receiver bias electrode 39a, bonded to a TFT substrate 34 via an adhesive 66 and electrically coupled to TFT pixel circuits 32 on the TFT substrate 34, as described above. An ultrasonic transmitter, including a metallized piezoelectric transmitter layer 22, is bonded to the opposite side of the TFT substrate 34 by an adhesive 68, as also described above. As described further below, both the receiver and transmitter electrodes are electrically connected at the front (receiver) side of the TFT substrate 34.

First turning to FIG. 10A, a metallized piezoelectric transmitter layer 22 is wrapped around a TFT substrate 34 to connect to its front surface. The TFT substrate 34 includes first and second transmitter bond pads 33a and 33b for connecting the electrodes to conductive routing (not shown) on the TFT substrate 34. The conductive routing provides an electrical connection to an FPC 90 via a FOG pad 35 and an ACF 96 overlying the FOG pad 35. The first transmitter electrode 24a contacts an ACF 96 overlying the first transmitter bond pad 33a. A conductive via 81 can extend through the piezoelectric transmitter layer 22 to electrically connect the second transmitter electrode 26a to the ACF 96, which also overlies the second transmitter bond pad 33b. According to various implementations, the conductive via 81 may be filled with conductive material or may have sidewalls coated with a conductive material. A receiver bias electrode lead 39b can be a conductive adhesive material such as silver epoxy or silver ink, for example, that can be dispensed, screen printed, or ink jet printed to connect a receiver bias electrode 39a to a receiver bond pad 33c. While in some implementations receiver bias electrode lead 39b may include one or more wires or traces that extend from receiver bias electrode 39a forming a separation from the piezoelectric receiver layer 36 (as shown), in some implementations a portion of the receiver bias electrode lead 39b may traverse or flow along a side of the receiver bias electrode 39a and/or along a side of the piezoelectric receiver layer 36 (not shown). In some implementations, the receiver bias electrode lead 39b may connect to a portion of the side of receiver bias electrode 39a, with little or none of the receiver bias electrode lead 39b extending over the top surface of receiver bias electrode 39a. In some implementations, the receiver bias electrode lead 39b may include or consist of a filled, partially filled, or unfilled via through the piezoelectric receiver layer 36 in a manner similar to the conductive via 81 described above. The conductive vias 81 may be circular, square, rectangular, or other suitable shape. In some implementations, receiver bias electrode lead 39b may be formed on the side of or through one or more slits, slots, holes, partial holes, or cutouts in the piezoelectric receiver layer 36. In some implementations, a portion of a conductive trace above or below the piezoelectric receiver layer 36 may extend beyond the layer 36 and be connected to the TFT substrate 34 or FPC 90. In some implementations, a portion of a conductive trace on the top or bottom of the FPC 90 may be connected to the receiver bias electrode layer 39a using a conductive epoxy, silver-urethane ink or other conductive material, with or without an underlying trace or bond pad on the TFT substrate 34. A conductive epoxy or other suitably conductive material may be used to connect patterns or traces on the piezoelectric receiver layer 36 to an underlying trace or pad on the TFT substrate 34. Conductive routing on the TFT substrate 34 can connect the receiver bond pad 33c to the FPC 90 via the FOG pad 35 and the ACF 96 overlying the FOG pad 35. In this manner, the transmitter and/or receiver may be connected to a COF-attached ASIC 92 disposed on the FPC 90. A stiffener 94 on the FPC 90 is also depicted in FIG. 10A. In some implementations, the receiver bias electrode lead 39b may flow between the receiver bias electrode lead 39b and traces and/or vias in the FPC 90, augmented by electrical traces and/or pads on the TFT substrate 34. Alternatively, the receiver bias electrode lead 39*b* may flow to connect the receiver bias electrode 39*a* directly to electrical traces and/or vias in the FPC 90, thereby simplifying the electrical circuit and circumventing the need for a receiver bond pad 33*c*. While transmitter bond pads 33*a* and 33*b* and receiver bond pad 33*c* are shown opposite FOG pad 35 on TFT substrate 34 in FIG. 10A, it is understood that one or more transmitter or receiver bond pads 33*a*-33*c* may be positioned elsewhere on TFT substrate 34, such as near FPC 90. Note that the techniques described for making electrical connections to the receiver bias electrode 39*a* may also be used for connections to the transmitter electrodes 24*a* and/or 26*a* here and elsewhere.

In the example of FIG. 10B, the metallized piezoelectric transmitter layer 22 is wrapped around the TFT substrate 34 to connect to its front surface. The first transmitter electrode 24*a* contacts an ACF 96 overlying the first transmitter bond pad 33*a*, as in FIG. 10A. The second transmitter electrode 26*a* may be connected to the second transmitter bond pad 33*b* by a conductive adhesive 83 such as silver epoxy or silver ink. The conductive adhesive 83 can be dispensed or ink jet printed, for example.

In the example of FIG. 10C, all connections from the transmitter and receiver bond pads 33*a*, 33*b*, and 33*c* may be made with ACF 96, with the second transmitter electrode 26*a* connected to the ACF 96 through a conductive via 81 as in FIG. 10A.

Figure 11B:
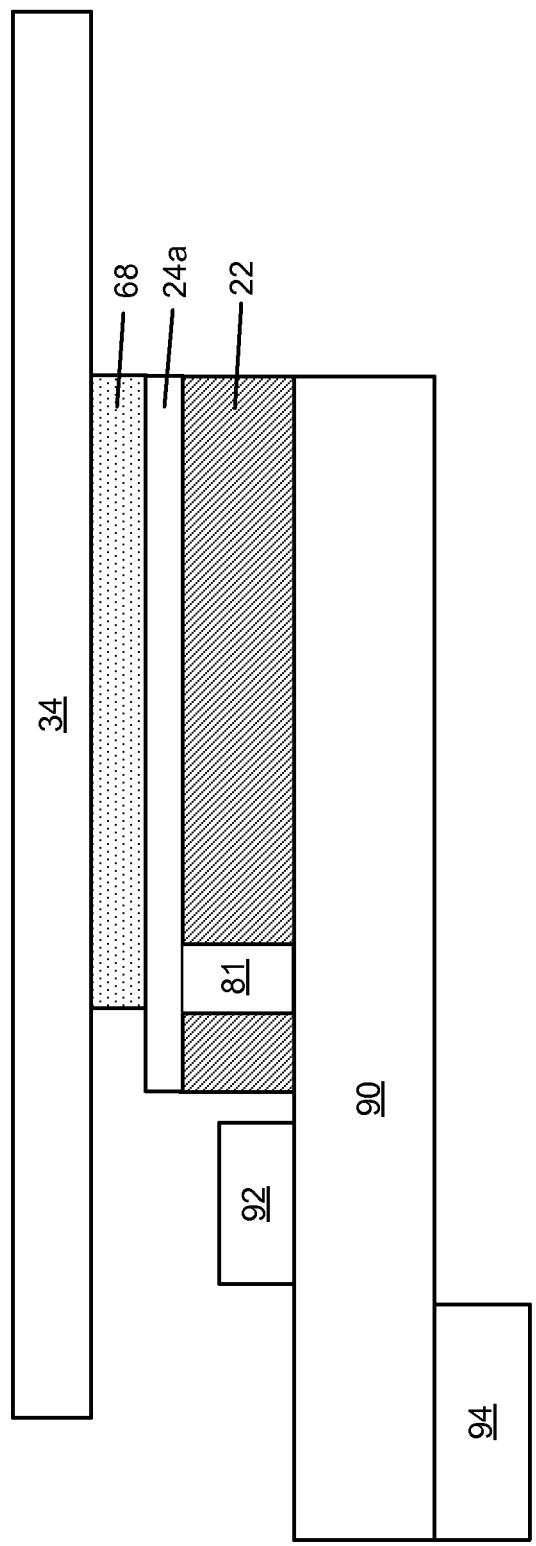

As indicated above, in some implementations, an FPC may overlay or underlay an ultrasonic transmitter or receiver. In such implementations, an electrode of the FPC may be in direct electrical communication with the metallized electrode of a piezoelectric layer or with the piezoelectric layer itself. FIGS. 11A and 11B show examples of implementations in which an electrode of a flexible printed circuit is in direct electrical communication with a piezoelectric layer of an ultrasonic sensor. It should be noted that in some implementations, an electrode in the FPC may be separated from the piezoelectric layer by a thin insulating layer. For example, an insulating layer of 0.1 μm to 20 μm between an electrode in the FPC and the piezoelectric layer would permit electrical communication between the two.

FIG. 11A shows the FPC 90 overlaying a piezoelectric receiver layer 36, which is bonded to a TFT substrate 34 via an adhesive 66 and electrically coupled to TFT pixel circuits 32. Note that unlike the implementations shown in the previous Figures, the piezoelectric receiver layer 36 is not metallized. The FPC 90 is bonded to a platen 40 by an adhesive 73. In some implementations, the FPC 90 may overlay and be attached to the piezoelectric receiver layer 36 by hot-press bonding and/or by using a separate adhesive. Temperatures during this attachment can be less than 85° C. in some implementations. The FPC 90 may be connected to conductive bond pads 33 on a TFT substrate 34 by ACF 96 or other appropriate conductive material. In this manner, connections to the FPC 90 can be made from the ultrasonic transmitter and/or other sensor components as described above. In this manner, connections can be made to a COF-attached ASIC 92 disposed on the FPC 90. A stiffener 94 on the FPC 90 is also depicted in FIG. 11A. In some implementations, an ultrasonic transmitter 20 (not shown) may be attached to the TFT substrate 34 on a side opposite TFT pixel circuits 32.

In the example of FIG. 11B, an FPC 90 is directly attached to a piezoelectric transmitter layer 22. In some implementations, the FPC 90 is attached to the piezoelectric transmitter layer 22 by hot-press bonding and/or by using a separate adhesive. Temperatures during this attachment can be less than 85° C. in some implementations. A piezoelectric transmitter layer 22 is metallized on one side with a first transmitter electrode 24*a*, which can connect to the FPC 90 through a conductive via 81, and be bonded to a TFT substrate 34 by an adhesive 68. In some implementations, a second transmitter electrode (not shown) of the ultrasonic transmitter is an electrode within or upon the FPC 90. In some implementations of the example of FIG. 11B, two FPCs may be employed, one bonded to the piezoelectric transmitter layer 22 as shown, and another bonded to the TFT substrate or to the piezoelectric receiver layer as described above. In some implementations, a piezoelectric receiver layer 36 may be attached to TFT pixel circuits 32 (not shown) on TFT substrate 34 opposite the piezoelectric transmitter layer 22.

Figure 12A:
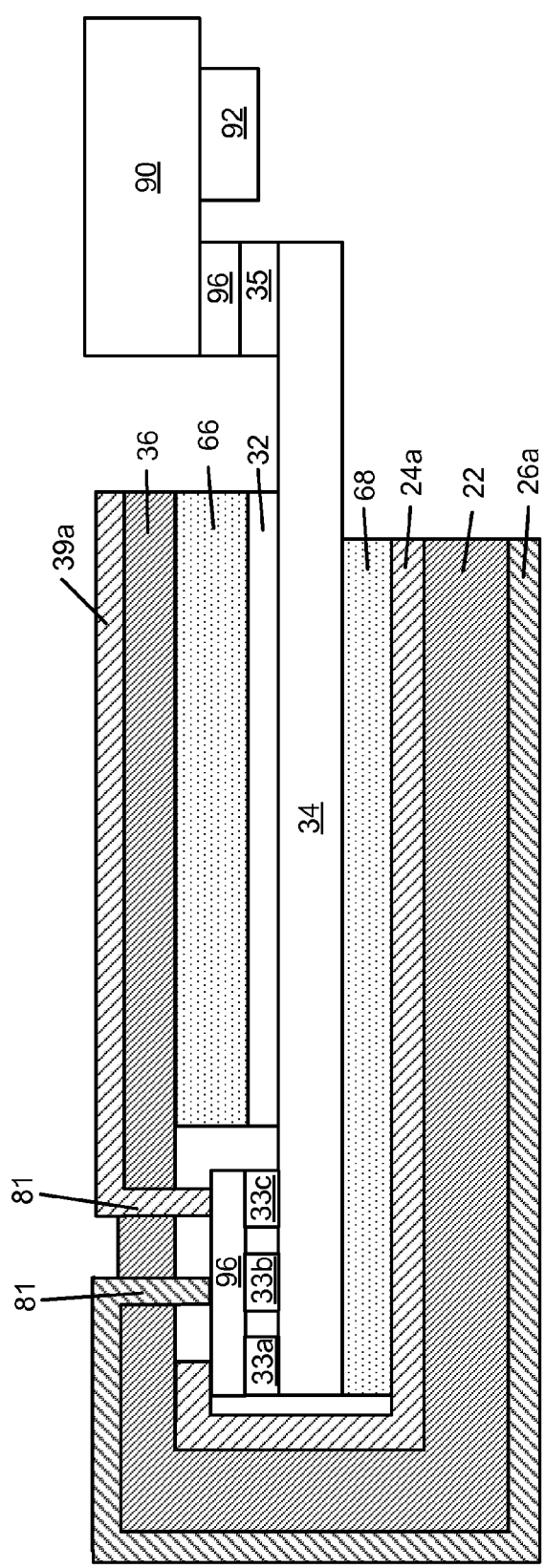
FIGS. 12A-12C show examples of ultrasonic sensors in which the same piezoelectric layer is used for both the receiver and the transmitter in a wrap-around configuration.
Figure 12B:
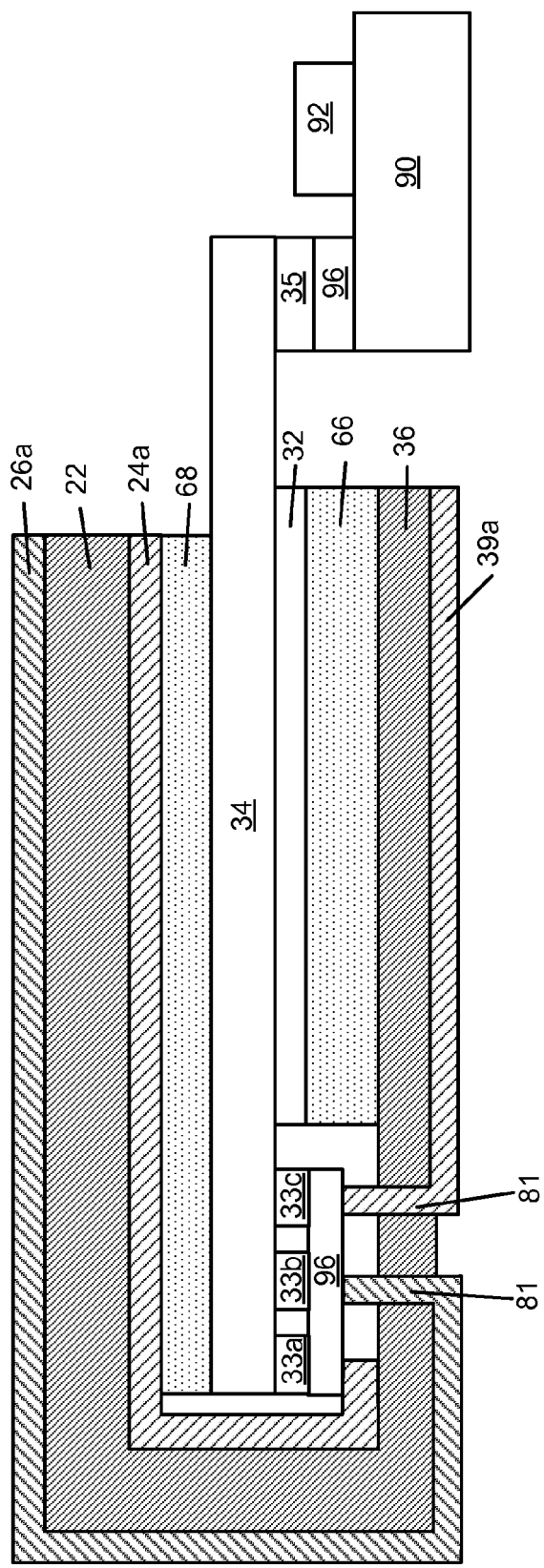
Figure 12C:
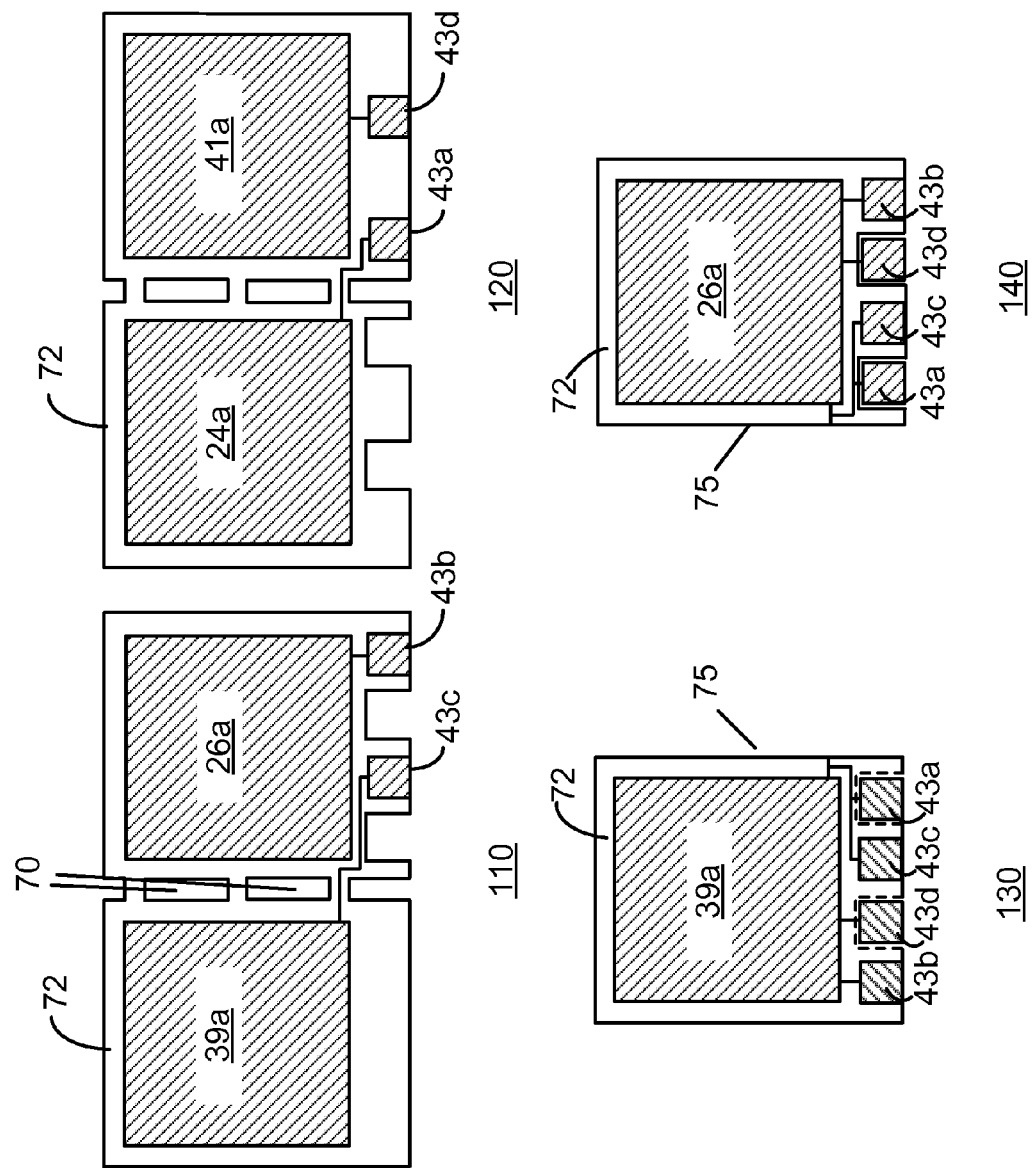

In some implementations, a piezoelectric layer may be wrapped around the TFT substrate to form both a piezoelectric transmitter layer 22 and a piezoelectric receiver layer 36. FIGS. 12A-12C show examples of ultrasonic sensors in which the same piezoelectric layer is used for both the receiver and the transmitter in wrap-around configurations.

FIG. 12A shows an example in which the TFT substrate 34 is oriented such that its top surface with TFT pixel circuits 32 is configured to face an overlying platen (not shown). The piezoelectric transmitter layer 22 and the piezoelectric receiver layer 36 are formed from a single piezoelectric layer, with the piezoelectric receiver layer 36 above the TFT substrate 34 and the piezoelectric transmitter layer 22 below the TFT substrate 34. As described above, the piezoelectric receiver layer 36 is electrically coupled to TFT pixel circuits 32 and bonded to the TFT substrate 34 by an adhesive 66. The piezoelectric transmitter layer 22 is metallized and bonded to the TFT substrate 34 by an adhesive 68.

An ACF 96 overlies first and second transmitter bond pads 33*a* and 33*b* and a receiver bond pad 33*c* on the TFT substrate 34 to electrically connect to the first and second transmitter electrodes 24*a* and 26*a* and the receiver bias electrode 39*a*. Conductive vias 81 may connect the second transmitter electrode 26*a* and the receiver bias electrode 39*a* to the ACF. Conductive routing on the TFT substrate 34 can connect the bond pads 33*a*, 33*b*, and 33*c* to an ASIC 92 on FPC 90 via a FOG pad 35 and an ACF 96 that overlies FOG pad 35.

FIG. 12B shows an example in which the TFT substrate is oriented such that the TFT pixel circuits 32 and the piezoelectric receiver layer 36 are below the TFT substrate 34 and the piezoelectric transmitter layer 22 is above the TFT substrate 34. An ACF 96 covers first and second transmitter bond pads 33*a* and 33*b* and a receiver bond pad 33*c* on the TFT substrate 34 to electrically connect to the first and second transmitter electrodes 24*a* and 26*a* and the receiver bias electrode 39*a*. Conductive vias 81 may connect the second transmitter electrode 26*a* and the receiver bias electrode 39*a* to the ACF. Conductive routing on the TFT substrate 34 can connect the bond pads 33*a*, 33*b*, and 33*c* to an ASIC 92 on FPC 90 via a FOG pad 35 and an ACF 96 that overlies FOG pad 35. In some implementations, a platen 40 (not shown) may be attached to the piezoelectric transmitter layer 22.

FIG. 12C shows an example of metallization of a PVDF piezoelectric layer to form a piezoelectric transmitter layer and a piezoelectric receiver layer. The example in FIG. 12C corresponds to a receiver on bottom and transmitter on top configuration. As shown in FIG. 12C, the piezoelectric layer 72 may include cutouts 70 to facilitate bending and forming. FIG. 12C depicts top and bottom views of the unfolded and folded metallized piezoelectric layer 72. First, at 110, a top view of the unfolded metallized piezoelectric layer 72 is shown, with the piezoelectric layer 72 metallized to form receiver bias electrode 39a and a second transmitter electrode 26a. In the example of FIG. 12C, metallization is nickel (Ni) on copper (Cu), though any appropriate metallization or conductive material including metal-impregnated polymers such as silver-urethane or silver ink may be used. Conductive routing and bond pads 43b and 43c, connected to the second transmitter electrode 26a and the receiver bias electrode 39a, respectively, are also shown. At 120, a bottom view of the unfolded metallized piezoelectric layer 72 is shown, with the piezoelectric layer 72 metallized to form receiver sense electrode 41a and a first transmitter electrode 24a. In some implementations, the receiver sense electrode 41a and related bond pad 43d are not formed. In some implementations, the first receiver sense electrode 41a includes an anisotropic conductive film such as ACF, an anisotropic conductive polymer, or a thin and lightly conductive layer such as APTES. In some implementations, receiver sense electrode 41a includes a patterned array of electrically isolated electrodes with a size and pitch that mates with underlying pixel input electrodes 38 of TFT pixel circuits 32. Conductive routing and bonds pads 43a and 43d, connected to the first transmitter electrode 24a and the receiver sense electrode 41a, respectively, are also shown. A top view of the folded piezoelectric layer 72 is shown at 130, with the receiver bias electrode 39a visible and the fold 75 indicated in the Figure. The bond pads 43a-43d are also shown. At 140, a bottom view of the folded piezoelectric layer 70 is shown with the second transmitter electrode 26a visible. Note that the folded views 130 and 140 show electrical traces on top of and through the folded metallized piezoelectric layer 72, as in some implementations the piezoelectric layer 72 is substantially optically transparent.

The implementations depicted in FIGS. 12A-12C offer low variation between the thickness of the piezoelectric transmitter layer and the thickness of the piezoelectric receiver layer, may allow the transmitter and receiver to be self-aligned, and allow a single-sided adhesive to be applied to bond a folded piezoelectric transmitter and receiver layer to the top and bottom of a TFT substrate. In some implementations, thin metal electrodes may be employed with thicker metal traces (e.g., silver ink).

Various adhesive layers are shown schematically in FIGS. 4 and 7A-12B to bond layers of the ultrasonic sensor together. In some implementations, these adhesives may be characterized in terms of one of three general classes of adhesives that may be employed. Adhesives 62, 64, 65, 66, 68, 69, 71, and 73 shown above in these Figures can bond metal to glass or plastic (e.g., a metal electrode to a TFT substrate, a spacer or a platen), metal to metal (e.g., a metal electrode to a metal electrode or cap), glass or plastic to glass or plastic (e.g., a glass or plastic spacer to a glass or plastic platen), or a flexible printed circuit to any of these materials. Examples of adhesives that may be used include pressure sensitive adhesives and epoxies. According to various implementations, adhesive layers disposed between the ultrasonic transmitter and/or ultrasonic receiver and the platen may be relatively thin, e.g., less than about 25 µm or less than about 10 µm to minimize acoustic reflection and absorption. In some implementations, the adhesive thickness may be less than about 5 µm or less than about 2 µm. In some implementations, the adhesive layer such as a PSA may have a removable liner on one or both sides prior to assembly. In some implementations, the adhesive may include a central backing layer with thin adhesive layers on each side of the backing layer, with one or more removable liners optionally attached to the outer surfaces of one or both adhesive layers prior to assembly. The adhesives may have a substantially uniform thickness for uniform acoustic reflections and absorption. For example, the thickness may vary by no more than +/−2 µm. Bonding is performed and the adhesive is selected to prevent formation of acoustic non-uniformities such as air bubbles or large variations in material density, thickness and speed of sound.

Adhesive 66 bonds the piezoelectric receiver layer to the TFT substrate, and may have the same properties as described above with respect to adhesives 62, 64, 65, 68, 69, 71, and 73. As discussed above, vertically electrically conductive adhesives such as ACF and highly resistive (lightly conductive) adhesives such as APTES may be employed. In some implementations the adhesive may have a lateral resistance of at least about 6 MΩ-cm, or at least about 10 MΩ-cm. In some implementations, the adhesive may be lightly conductive with a resistivity larger than about 1 MΩ-cm.

Adhesive 65 can bond the metal backside cap to the TFT substrate. As such, it has high cohesive strength and provides reliable adhesion to the TFT substrate. Examples include pressure sensitive adhesives and epoxies. The same material may also be used for adhesive 71 that bonds the metal cap to the ultrasonic transmitter, in some implementations. These bonds may be coated with one or more protective layers to reduce the ingress of moisture into the layers of the sensor.

Figure 13A:
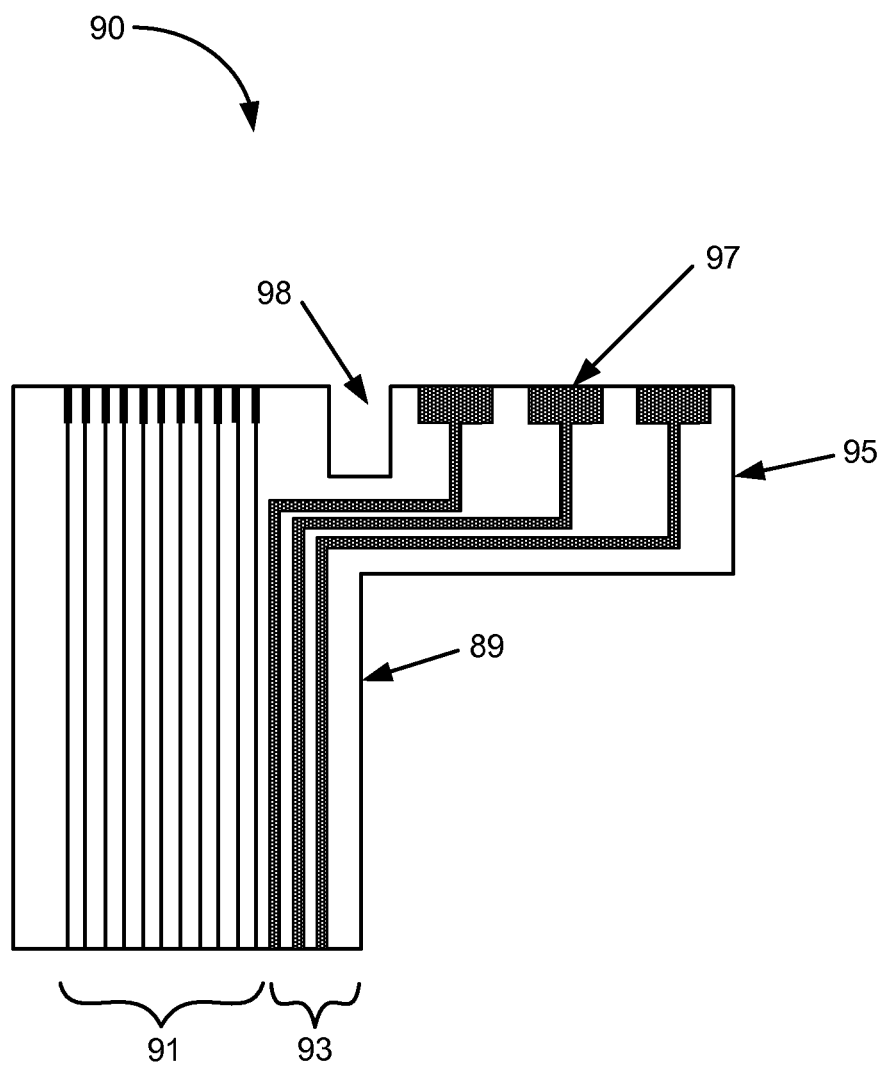
FIG. 13A shows an example of a schematic illustration of a flexible printed circuit configured to wrap around a thin film transistor substrate.

FIG. 13A shows an example of a schematic illustration of a flexible printed circuit configured to wrap around a TFT substrate. An FPC 90 may include a flexible cable 89 having control and data traces 91 and low-resistance piezoelectric transmitter and receiver traces 93 printed or otherwise formed thereon. The flexible cable 89 may include a wrap-around portion 95 on which the transmitter and receiver traces 93 connect to transmitter and receiver bond pads 97. A notch 98 or other feature may be included in the flexible cable 89 to separate the wrap-around portion 95 from the remainder of the flexible cable 89. The notch 98 may allow the flexible cable 89 to be more readily wrapped around a portion of a TFT substrate, avoid covering components or alignment marks, or to aid in alignment. In some implementations, one or more slits, slots or holes may serve as vias that are traversed or filled in with dispensed or otherwise applied conductive material, allowing electrical connections to be formed between one side of the flexible cable to another side or layer, or to an underlying substrate.

Figure 13B:
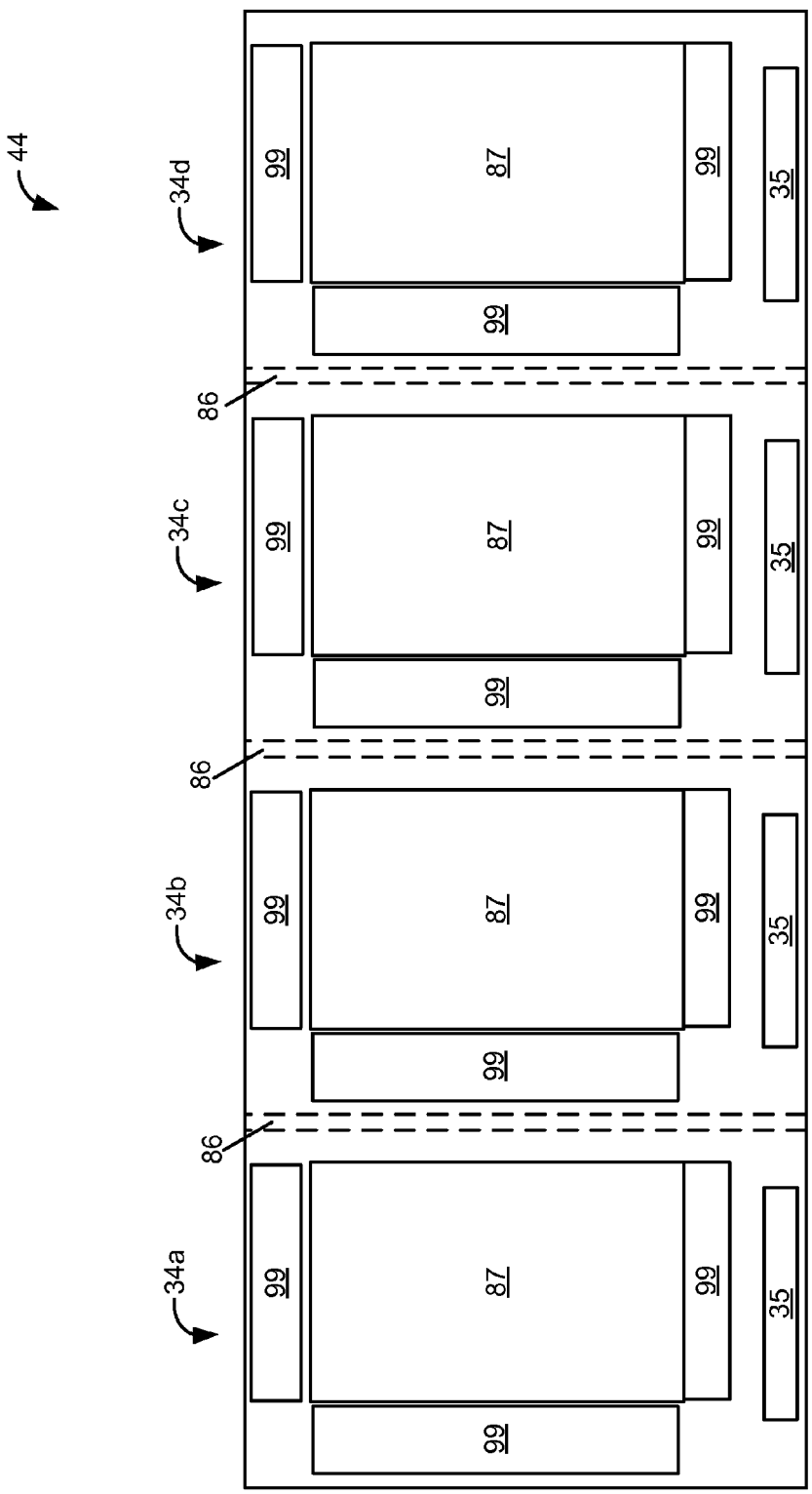
FIGS. 13B-13G show examples of schematic illustrations of various stages of a process for attaching flexible printed circuits to thin film transistor sensor arrays.
Figure 13C:
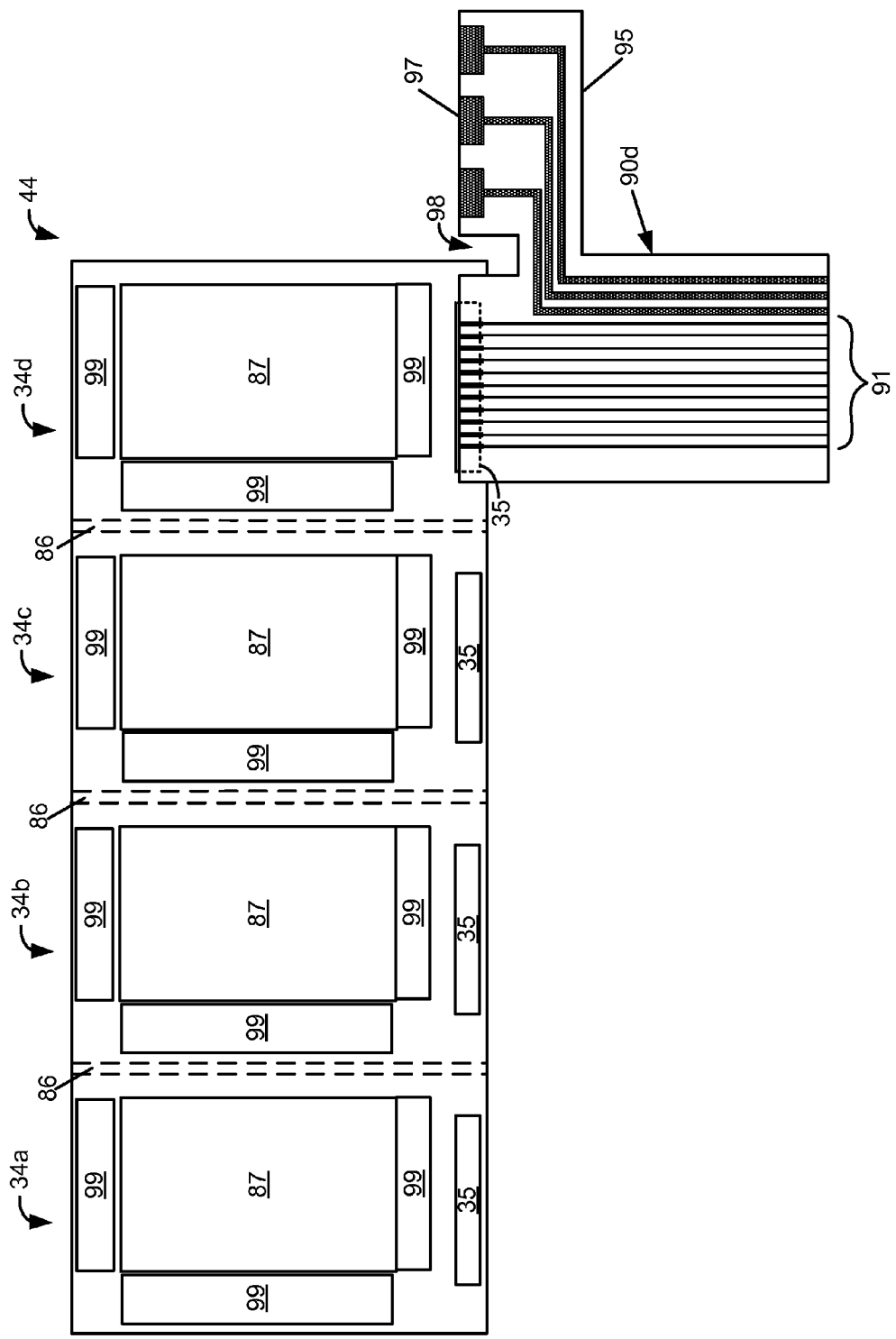

In some implementations, a flexible printed circuit such as the FPC 90 in FIG. 13A may be attached to a TFT substrate that is part of a strip of TFT substrates during an assembly process. FIGS. 13B-13G show examples of schematic illustrations of various stages of a process for attaching flexible printed circuits to thin film transistor sensor arrays. FIG. 13B shows an example of a strip 44 of TFT substrates 34a-34d. Each TFT substrate 34a-34d includes a central area 87 including an array of pixel circuits, one or more peripheral areas 99 for gate drivers, data storage, multiplexers, and additional circuitry as described above with reference to FIGS. 3A and 3B, and one or more FOG pads 35 for connecting to an FPC. The strip 44 is configured to be scribed in scribe regions 86 for singulating the TFT substrates 34a-34d. Prior to singulation, an FPC can be attached to each TFT substrate 34a-34d. FIG. 13C shows an example of an FPC 90d attached to the TFT substrate 34d by ACF 96. A notch 98 in the FPC 90d is aligned with an edge of the TFT substrate 34d. For the purposes of illustration, the ACF 96 is not shown in FIG. 13C, though it is disposed between the FOG pads 35 of the TFT substrate 34d (shown in FIG. 13B) and the FPC 90d. The ACF 96 physically connects the FPC 90d to the TFT substrate 34d, and may electrically connect control and data traces 91 of the FPC 90d to the FOG 35 of the TFT substrate 34d. The FPC 90d also includes a wrap-around portion 95 with transmitter and receiver bond pads 97 printed thereon. The wrap-around portion 95 is configured to wrap around to the opposite side of the TFT substrate 34d, with the transmitter and receiver bond pads 97 configured to connect to the TFT substrate 34d on that side. For example, the transmitter and receiver bond pads 97 may connect to a backside-mounted transmitter or to the leads from a transmitter and receiver pair.

Figure 13D:
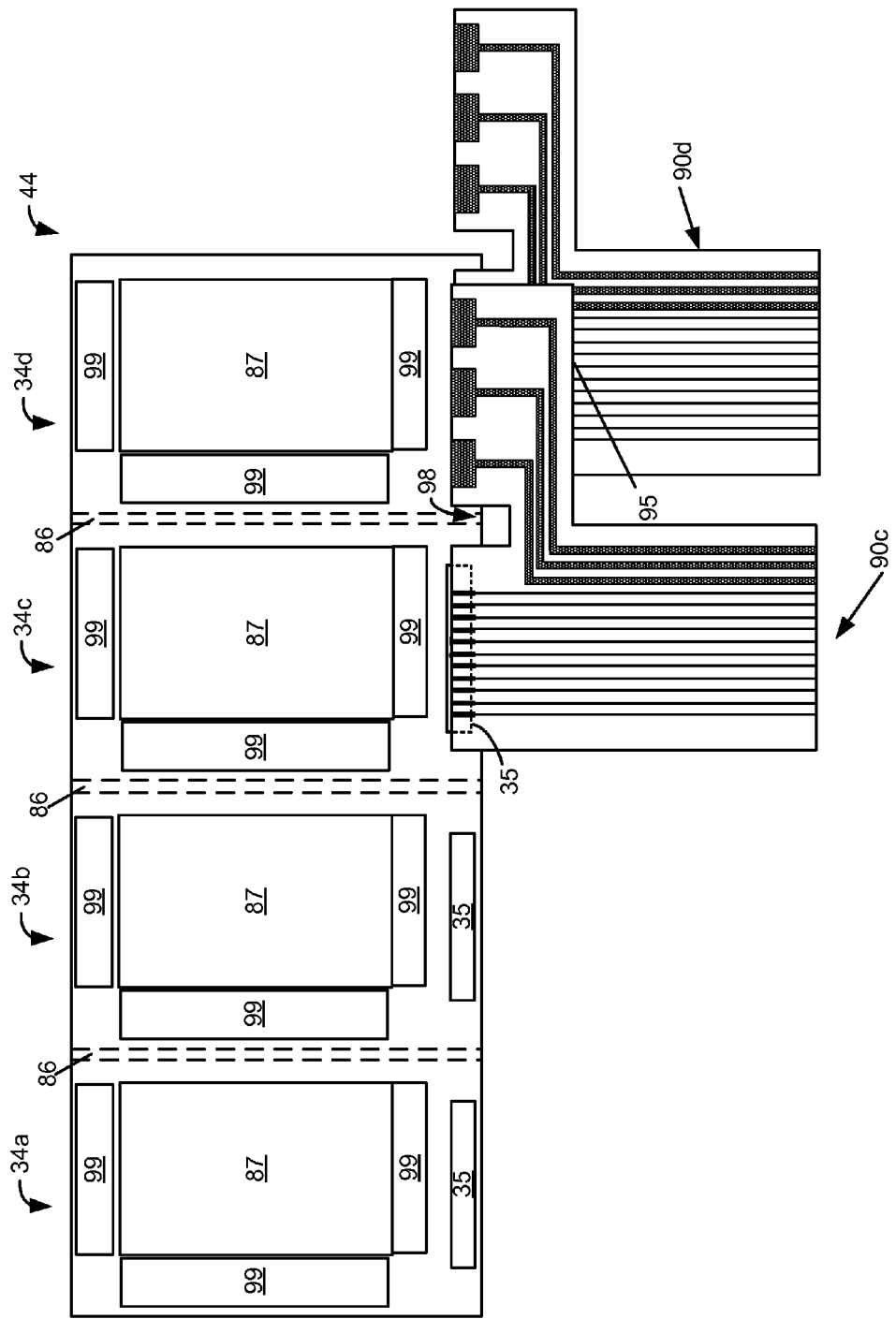

The assembly process can further involve attachment of FPCs to each of the TFT substrates 34a-34d in the strip 44 prior to singulation and wrap-around. FIG. 13D shows an example of an FPC 90c attached to FOG pads 35 of TFT substrate 34c by ACF 96 (not shown for clarity). A wrap-around portion 95 of the FPC 90c overlies but is not connected to the FPC 90d. A notch 98 in FPC 90c is aligned with the scribe region 86 that is between the TFT substrate 34c and the TFT substrate 34d. In this manner, the FPC 90c does not cover or obscure the scribe region 86.

Figure 13E:
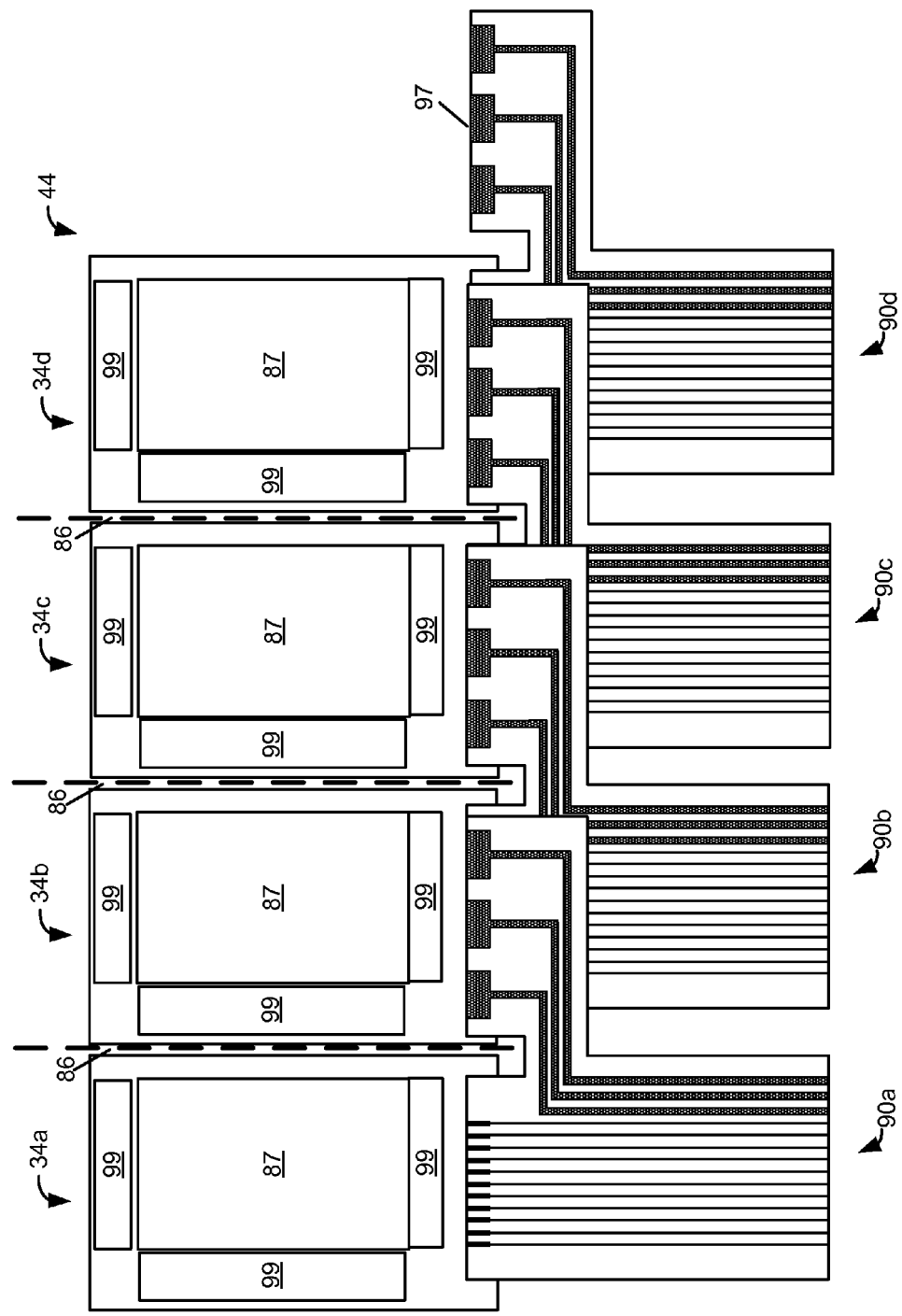
Figure 13F:
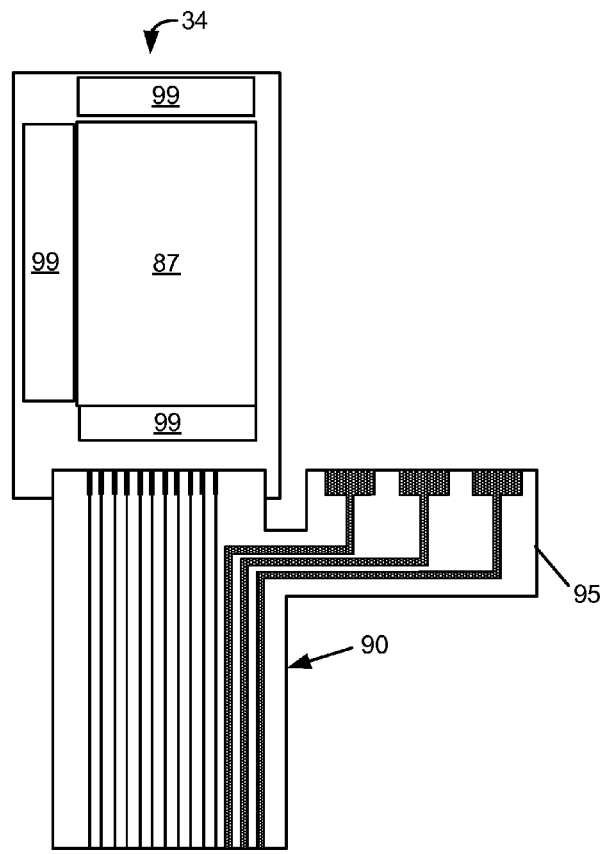
Figure 13G:
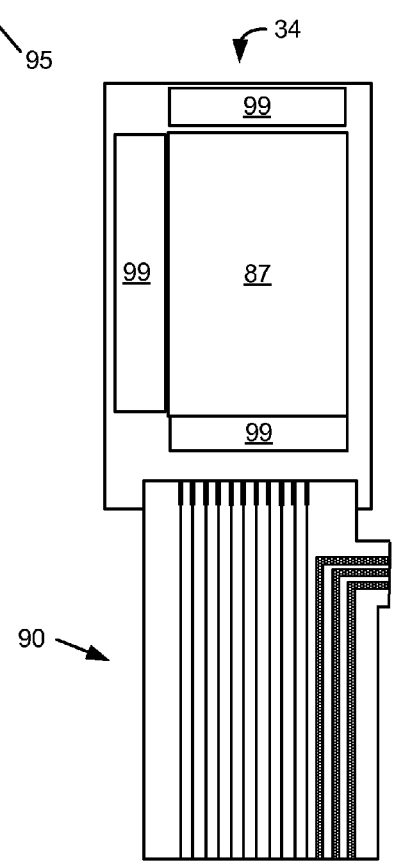

FIG. 13E shows an example of singulation of the TFT substrates 34a-34d. Each TFT substrate 34a-34d is shown attached to an FPC 90a-90d, with attachment performed as described above with respect to FIGS. 13C and 13D. Scribing is performed in the scribe regions 86 between each of TFT substrates 34a and 34b, TFT substrates 34b and 34c, and TFT substrates 34c and 34d as indicated by the dashed lines. Because the FPCs 90a-90d do not overlie any of the scribed regions 86, scribing does not involve cutting an FPC. FIG. 13F shows an example of a singulated TFT substrate 34 attached to an FPC 90 prior to wrapping a wrap-around portion 95 of the FPC 90 around the TFT substrate 34. FIG. 13G shows an example of the singulated TFT substrate 34 in FIG. 13E with the wrap-around portion 95 wrapped around the TFT substrate 34. In some implementations, the wrap-around portion may then be physically and/or electrically connected to the TFT substrate 34. The example assembly process illustrated in FIGS. 13B-13G can be performed, for example, as part of block 114 of FIG. 5 or block 126 of FIG. 6.

In some implementations, a portion of FPC 90 may be attached to the top side (circuit side) of TFT substrate 34 and another portion attached to the backside of TFT substrate 34, with a portion of the FPC 90 wrapping loosely or tightly around an edge of the TFT substrate 34. Another portion of the FPC 90 may extend away from the TFT substrate 34 for external electrical connections. The FPC 90 may have one or more active or passive components attached thereto, with the components positioned at one or more places along the FPC 90 including the portion near the top side of TFT substrate 34, the wrapped portion, the portion attached to the backside of TFT substrate 34, or the portion of FPC 90 extending away from the ultrasonic sensor assembly. Stiffeners may be added to FPC 90 at strategic locations, such as behind the ultrasonic transmitter layer or near connectors. Standoffs may be included on the FPC 90 to control the spacing between the FPC 90 and the piezoelectric transmitter. As noted above, FPC 90 may be single or multi-layer to accommodate the active components, passive components, and connectors.

One or more operations of the fabrication methods described in this disclosure can be implemented in apparatus including one or more stations or modules for placing one or more components, bonding two or more components together, and dispensing conductive inks or epoxies, and a controller including program instructions for conducting a process. A module for vacuum bonding may include a vacuum chamber and gas inlets, outlets, pumps for establishing and maintaining a vacuum, a pressure plate or diaphragm and a shelf that may function as an anvil, and a heater for controlling temperature. A module for lamination may include a movable press, gas inlets, outlets, a rotating cylinder for feeding the parts to be laminated at a controlled feed rate, air pressure cylinders for applying pressure to the rotating cylinder, and a heater for controlling temperature. A module for dispensing may include a dispenser and one or more sensors for detecting alignment, a controllable X-Y stage, a syringe, and an air pressure cylinder or positive displacement mechanism attached to the syringe. In some implementations, a controller may include one or more memory devices and one or more processors configured to execute the program instructions so that the apparatus can perform a method in accordance with the disclosed implementations. The processor may include a central processing unit (CPU) or a computer, analog and/or digital input/output connections, motor controller boards, and other like components. Program instructions for implementing appropriate process operations may be executed on or by the processor. These program instructions may be stored on the memory devices or other machine-readable media associated with the controller or they may be provided over a network.

In some implementations, the controller may control all, most, or a subset of the operations of an apparatus. For example, the controller may control all or most the operations of an associated with dispensing of a conductive ink or laminating an adhesive. The controller may execute system control software including sets of instructions for controlling the timing of the process operations, pressure levels, temperature levels and other parameters of particular manufacturing processes further described with respect to FIGS. 5 and 6. In some implementations, other computer programs, scripts, or routines stored on memory devices associated with the controller may be employed.

In some implementations, a user interface may be associated with the controller. The user interface may include a display screen, graphical software to display process conditions, and user input devices such as pointing devices, keyboards, touch screens, microphones, and other like components.

In some implementations, the program instructions for controlling the operations of an apparatus may include computer program code written in any conventional computer readable programming language, such as, for example, assembly language, C, C++, Pascal, Fortran, or others. Compiled object code or script may be executed by the processor of the controller to perform the tasks identified in the program instructions.

In some implementations, signals for monitoring a manufacturing process may be provided by analog and/or digital input connections of the controller. Signals for controlling a manufacturing process may be output on analog and/or digital output connections of the controller.

The various illustrative logics, logical blocks, modules, circuits and algorithm steps described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and steps described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some implementations, particular steps and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also can be implemented as one or more computer programs, i.e., one or more modules of computer program instructions, encoded on a computer storage media for execution by or to control the operation of apparatus.

If implemented in software, the functions may be stored on or transmitted over as one or more instructions or code on a computer-readable medium. The steps of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and blue-ray disc where disks usually reproduce data magnetically, while discs reproduce data optically with lasers. Combinations of the above also may be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein. The word "exemplary" is used exclusively herein to mean "serving as an example, instance, or illustration." Any implementation described herein as "exemplary" is not necessarily to be construed as preferred or advantageous over other possibilities or implementations. Additionally, a person having ordinary skill in the art will readily appreciate, the terms "upper" and "lower" are sometimes used for ease of describing the figures, and indicate relative positions corresponding to the orientation of the figure on a properly oriented page, and may not reflect the proper orientation of a device as implemented.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, a person having ordinary skill in the art will readily recognize that such operations need not be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

What is claimed is:

1. An apparatus comprising:
an ultrasonic transmitter for generating ultrasonic energy;
a platen; and
an ultrasonic receiver for detecting ultrasonic energy including:
an array of thin film transistor (TFT) pixel circuits disposed on a TFT substrate;
a piezoelectric receiver layer having first and second opposing surfaces, the first surface bonded with an adhesive to the TFT substrate and to the TFT pixel circuits; and
a receiver bias electrode overlying the second surface of the piezoelectric receiver layer, wherein the piezoelectric receiver layer is in electrical communication with the TFT pixel circuits, wherein the piezoelectric receiver layer is capacitively or resistively coupled through the adhesive with the TFT pixel circuits.

2. The apparatus of claim 1, further comprising a spacer layer bonded between the platen and the ultrasonic receiver.

3. The apparatus of claim 1, wherein the piezoelectric receiver layer is disposed between the platen and the TFT substrate and the ultrasonic transmitter is on the opposite side of the TFT substrate as the piezoelectric receiver layer.

4. The apparatus of claim 1, wherein the piezoelectric receiver layer is disposed between the platen and the TFT substrate and the ultrasonic transmitter is on the same side of the TFT substrate as the piezoelectric receiver layer.

5. The apparatus of claim 1, wherein the TFT substrate is disposed between the platen and the piezoelectric receiver layer and the ultrasonic transmitter is on the opposite side of the TFT substrate as the piezoelectric receiver layer.

6. The apparatus of claim 1, wherein the TFT substrate is disposed between the platen and the piezoelectric receiver layer and the ultrasonic transmitter is on the same side of the TFT substrate as the piezoelectric receiver layer.

7. The apparatus of claim 1, further comprising a protective cap on the opposite side of the TFT substrate as the platen and bonded to the TFT substrate.

8. The apparatus of claim 1, further comprising a flexible printed circuit bonded to the TFT substrate.

9. The apparatus of claim 1, wherein the receiver bias electrode is disposed on a flexible printed circuit.

10. The apparatus of claim 1, wherein the ultrasonic transmitter includes a piezoelectric transmitter layer having first and second opposing surfaces, a first transmitter electrode overlying the first surface and a second transmitter electrode overlying the second surface.

11. The apparatus of claim 10, wherein the one of the first and second transmitter electrodes is disposed on a flexible printed circuit.

12. An apparatus comprising:
    an ultrasonic receiver for detecting ultrasonic energy including:
        an array of thin film transistor (TFT) pixel circuits disposed on a TFT substrate;
        a piezoelectric layer having first and second opposing surfaces, the first surface bonded with an adhesive to the TFT substrate and to the TFT pixel circuits; and
        a receiver bias electrode overlying the second surface of the piezoelectric layer;
    wherein the piezoelectric layer is in electrical communication with the TFT pixel circuits, wherein the piezoelectric receiver layer is capacitively or resistively coupled through the adhesive with the TFT pixel circuits.

13. The apparatus of claim 12, wherein the adhesive has a lateral resistivity of at least 1 MΩ-cm.

14. The apparatus of claim 12, wherein the adhesive is selected from an anisotropic conductive film (ACF) and (3-Aminopropyl)triethoxysilane (APTES).

15. The apparatus of claim 12, wherein the adhesive has a thickness of no more than about 10 μm.

16. The apparatus of claim 12, further comprising a flexible printed circuit (FPC) overlying the second surface of the piezoelectric layer, wherein the FPC includes the receiver bias electrode.

17. The apparatus of claim 16, wherein the FPC is bonded to one or more conductive pads on the TFT substrate.

18. An apparatus comprising:
    an ultrasonic transmitter for generating ultrasonic energy;
    a platen; and
    an ultrasonic receiver for detecting ultrasonic energy including:
        an array of thin film transistor (TFT) pixel circuits disposed on a TFT substrate;
        a piezoelectric receiver layer having first and second opposing surfaces, the first surface bonded with an adhesive to the TFT substrate and to the TFT pixel circuits; and
        a receiver bias electrode overlying the second surface of the piezoelectric receiver layer, wherein the piezoelectric receiver layer is in electrical communication with the TFT pixel circuits, wherein the TFT substrate is disposed between the platen and the piezoelectric receiver layer and the ultrasonic transmitter is on the opposite side of the TFT substrate as the piezoelectric receiver layer.

19. An apparatus comprising:
    an ultrasonic transmitter for generating ultrasonic energy;
    a platen; and
    an ultrasonic receiver for detecting ultrasonic energy including:
        an array of thin film transistor (TFT) pixel circuits disposed on a TFT substrate;
        a piezoelectric receiver layer having first and second opposing surfaces, the first surface bonded with an adhesive to the TFT substrate and to the TFT pixel circuits; and
        a receiver bias electrode overlying the second surface of the piezoelectric receiver layer, wherein the piezoelectric receiver layer is in electrical communication with the TFT pixel circuits, wherein the TFT substrate is disposed between the platen and the piezoelectric receiver layer and the ultrasonic transmitter is on the same side of the TFT substrate as the piezoelectric receiver layer.

* * * * *